United States Patent
Hodrinsky et al.

(10) Patent No.: US 11,666,451 B2
(45) Date of Patent: Jun. 6, 2023

(54) BIO-MECHANICALLY COMPATIBLE 3D-PRINTED INTERVERTEBRAL DISC

(71) Applicants: Todd Hodrinsky, Mansfield Center, CT (US); Marcel Janse, Hasselt (BE)

(72) Inventors: Todd Hodrinsky, Mansfield Center, CT (US); Marcel Janse, Hasselt (BE)

( * ) Notice: Subject to any disclaimer, the term of this patent is extended or adjusted under 35 U.S.C. 154(b) by 0 days.

(21) Appl. No.: 17/712,065

(22) Filed: Apr. 1, 2022

(65) Prior Publication Data

US 2022/0331124 A1   Oct. 20, 2022

Related U.S. Application Data

(63) Continuation-in-part of application No. 17/035,582, filed on Sep. 28, 2020, now abandoned.

(60) Provisional application No. 62/906,858, filed on Sep. 27, 2019.

(51) Int. Cl.
| | |
|---|---|
| *A61F 2/44* | (2006.01) |
| *A61B 6/03* | (2006.01) |
| *A61B 34/10* | (2016.01) |
| *B33Y 80/00* | (2015.01) |
| *A61F 2/30* | (2006.01) |

(52) U.S. Cl.
CPC ............. *A61F 2/4425* (2013.01); *A61B 6/03* (2013.01); *A61B 34/10* (2016.02); *A61B 2034/107* (2016.02); *A61F 2002/30107* (2013.01); *A61F 2002/443* (2013.01); *A61F 2220/005* (2013.01); *A61F 2220/0058* (2013.01); *A61F 2310/00047* (2013.01); *A61F 2310/00179* (2013.01); *B33Y 80/00* (2014.12)

(58) Field of Classification Search
None
See application file for complete search history.

(56) References Cited

U.S. PATENT DOCUMENTS

| | | | | |
|---|---|---|---|---|
| 2009/0125033 | A1* | 5/2009 | Hushka | A61B 17/1671 606/99 |
| 2012/0191189 | A1* | 7/2012 | Huang | A61F 2/4425 623/17.11 |
| 2015/0289990 | A1* | 10/2015 | Bertele | A61F 2/30771 29/527.1 |
| 2022/0039965 | A1* | 2/2022 | Casey | A61F 2/4425 |

* cited by examiner

*Primary Examiner* — Mohammad M Ameen

(74) *Attorney, Agent, or Firm* — Alexander Postnikov

(57) ABSTRACT

An artificial replacement disk assembly comprised of a core in between two endplates. The endplates have outer surfaces that match the surface morphologies of the corresponding vertebral endplates. The endplates may have textured inner surface to form a strong fusion with the core during the fabrication process. The thick solid endplates strongly fused to the core create a very resilient implant. Gripping structures on the endplates may permit easy manipulation of the assembly during surgical procedures.

19 Claims, 27 Drawing Sheets

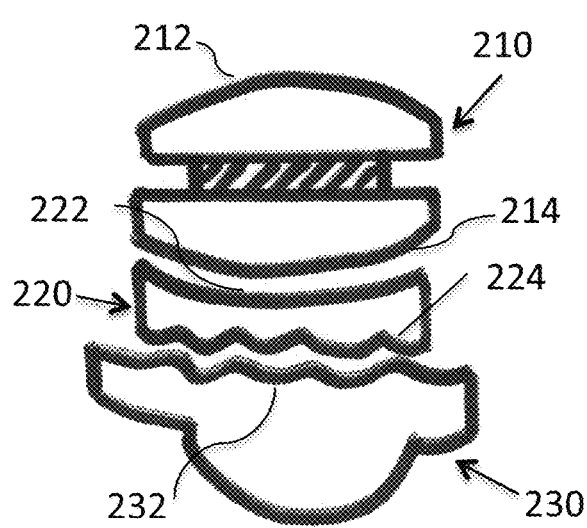
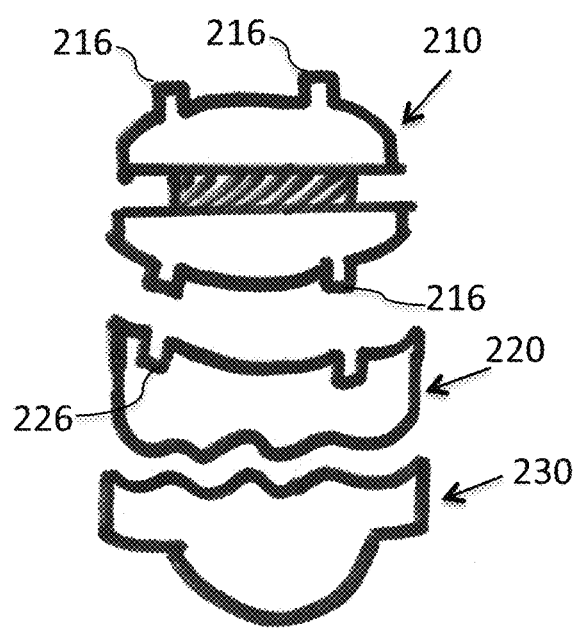
FIG. 2A
FIG. 2B

BIO-MECHANICALLY COMPATIBLE 3D-PRINTED INTERVERTEBRAL DISC

CROSS-REFERENCE TO RELATED APPLICATIONS

This application claims the benefit of and is a Continuation-in-part of U.S. non-provisional application Ser. No. 17/035,582, filed on Sep. 28, 2020, the content of which is incorporated in its entirety. This application further claims the benefit of U.S. provisional patent application No. 62/906,858 filed on Sep. 27, 2019, the content of which is incorporated by reference in its entirety.

FIELD OF THE INVENTION

This invention relates generally to artificial disc replacement and fusion devices, and more specifically to biomechanically compatible 3D-printed implant devices for human and animal spines.

BACKGROUND OF THE INVENTION

There are several artificial disc replacement and fusion devices available on the market today for spinal correction procedures, replacing damaged cushioning tissue—called vertebral disc—located between the vertebrae, as illustrated in FIG. 1A. The replacement must be safe to implant, reliable and long lasting.

With an artificial disc replacement procedure, the implant must replicate the movement of a natural disc. With a fusion procedure, the implant must lock the vertebrae in place permanently. Some examples include the Bryan cervical artificial disc and the Charite lumbar artificial disc by Medtronic, the M6 disc by Spinal Kinetics, and the ESP disc by FH Orthopedics.

Typically, the disc replacement procedure is performed under general anesthesia with the help of X-ray imaging technology. While holding the disc space between the two vertebrae open, the disc is removed using a microscope and surgical instruments specifically made for this purpose. Once the disc has been safely removed, the space is increased to restore the natural height and to allow the implant to be inserted. The endplates (top and bottom of each vertebrae) are then prepared to incorporate the artificial disc or fusion device. When the artificial disc or fusion device is firmly in place, the tension is taken off the vertebral bodies above and below, thereby recompressing the artificial disc or fusion device and thus holding it in place, as illustrated in FIG. 1B for an artificial disc device or in FIG. 1C for a fusion device.

Typically, the implants are made of metal such as titanium, to promote ingrowth of bony material for long-term stability. However, this procedure carries some risks associated with milling and shaping of the endplates, which could result in potential damage of nearby discs, nerves, blood vessels, joints and the vertebral bodies. Moreover, the mismatch between the surface morphology of the implant and that of the bone endplates could potentially cause a poor connection potentially resulting in loosening of the prosthesis, potential subsidence, as well as non-uniform ingrowth of bony material, hence affecting the long-term stability of the implant. The embodiments and methods of the present invention solve the above-mentioned problems associated with the artificial disc replacement and fusion devices and procedures by incorporating a 3D printed implant device, which matches the mating surface of the implant and the surface morphology of the bone endplates, thereby eliminating the need of milling and shaping, preventing loosening of the disc, increasing its immediate post-operative and long-term stability.

SUMMARY OF THE EMBODIMENTS

In one aspect, an interface device includes a first surface that matches the surface morphology of the corresponding artificial disc and a second surface that matches the surface morphology of the corresponding endplate of the vertebrae. The interface device of the present disclosure can be fabricated using three-dimensional additive manufacturing printing technology.

A method for fabricating an interface device includes acquiring three-dimensional image scan data of spine or neck using computerized tomography (CT) scan or magnetic resonance imaging (MM) or both, converting the CT and/or MM scan to an engineering file, creating a three-dimensional digital model of a vertebrae's endplate, obtaining a three-dimensional digital model of a corresponding mating surface of the artificial replacement disc, combining the three-dimensional digital model of the vertebrae's endplate and three-dimensional digital model of the mating surfaces of the artificial replacement disc, outputting the combined three-dimensional digital model, and printing the interface device.

According to the present disclosure, a method for directly printing an interface device on the surface of an artificial disc includes acquiring 3D image scan data of spine or neck using Computerized Tomography (CT) scan and/or Magnetic Resonance Imaging (MRI) scan, converting the CT and/or MRI scan to an engineering file, creating a 3D digital model of the vertebrae's endplate, obtaining a 3D digital model of the corresponding matting surfaces of the artificial replacement disc, combining the 3D digital model of the vertebrae's endplate and the 3D digital model of the matting surfaces of the artificial replacement disc, outputting the combined 3D digital model, positioning the artificial replacement disc on a printing tray of a 3D printer, and printing the interface device on the surface of the artificial replacement disc.

Further according to the present disclosure, a method for fabricating an artificial replacement disk comprises the steps of acquiring three-dimensional image scan data of spine or neck using at least one of computerized tomography (CT) scan and magnetic resonance imaging (MRI), converting the CT and/or MRI scan to an engineering file, creating a three-dimensional digital model of a target disc space in between a superior vertebrae and an inferior vertebrae, printing a first endplate and a second endplate, and injection molding a core in between the first inner surface and the second inner surface to create the artificial replacement disk assembly.

Further according to the present disclosure, a method of fabricating an artificial replacement disk comprises the steps of acquiring three-dimensional image scan data of spine or neck using at least one of computerized tomography (CT) scan and magnetic resonance imaging (MRI), converting the CT and/or MRI scan to an engineering file, creating a three-dimensional digital model of a target disc space in between a superior vertebrae and an inferior vertebrae, printing a first endplate and a second endplate, molding a core, fusing the core to the endplates to create the artificial replacement disk assembly.

Other aspects, embodiments and features of the device and method of the present invention will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the device and method shown where illustration is not necessary to allow those of ordinary skill in the art to understand the device and method.

BRIEF DESCRIPTION OF THE DRAWINGS

The preceding summary, as well as the following detailed description of the disclosed device and method, will be better understood when read in conjunction with the attached drawings. It should be understood, however, that neither the device nor the method is limited to the precise arrangements and instrumentalities shown.

FIGS. 2A and 2B are schematic illustration of the artificial disc interface device in accordance with the embodiments of the present disclosure.

DETAILED DESCRIPTION OF SPECIFIC EMBODIMENTS

Figure 1A:
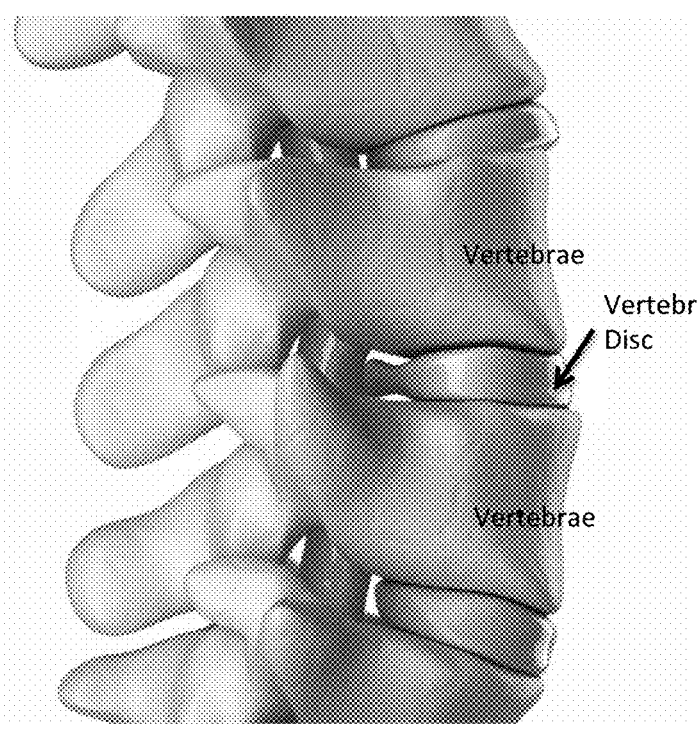
FIGS. 1A-1C illustrate a conventional method of vertebral disc replacement.
Figure 1B:
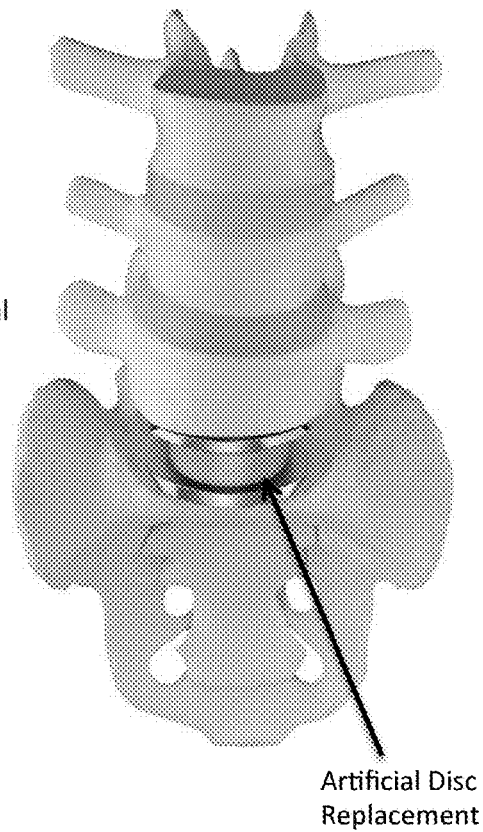
Figure 1C:
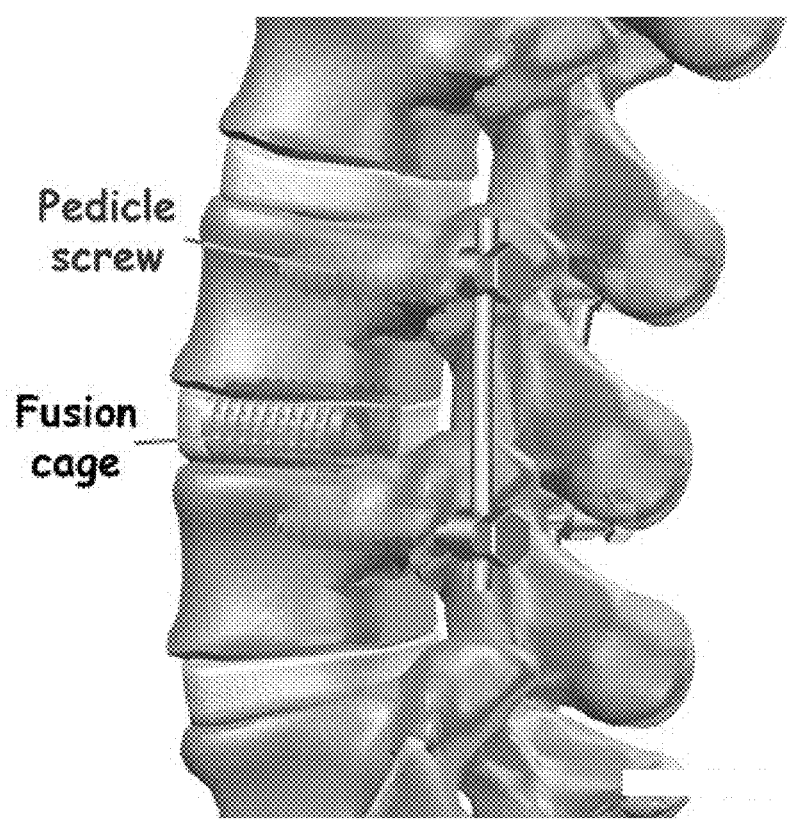

As shown in FIG. 2A, the interface device 220 of the present disclosure, positioned between artificial replacement disc 210 and vertebrae 230, is designed to match surface morphology of the corresponding mating surfaces of the replacement disc and the vertebrae. Hence, the top surface 222 of the interface device 220 conforms to the corresponding bottom surface 214 of the replacement disc 210 for mating the interface device with the artificial disc. Likewise, the bottom surface 224 of the interface device 220 conforms to the corresponding top surface (endplate) 232 of the vertebrae 230 for mating the interface device with the vertebrae.

In some other instances, when, for example, the artificial disc 210 includes tabs 216, as illustrated in FIG. 2B, the interface device is designed to include grooves 226 disposed to fit into corresponding tabs 216. It will be appreciated by a person skilled in the art that the top surface of the interface device can be designed to conform to any surface morphology of the corresponding surface of the artificial disc. If the disc includes grooves, then the interface device can include corresponding tabs for mating the disc with the interface device, etc.

In some instances, the artificial disc can be sandwiched between two interface devices, i.e., a second interface device can be disposed on top of the artificial disc, for mating with the top surface 212 of the artificial disc 210, wherein the top surface of the second interface device conforms to the surface morphology of the endplate of a second vertebrae (not shown).

In some embodiments, the interface device of the present invention can match the shape of the artificial disc, for example if the disc is oval, then the interface device is designed to be oval as well, or if the disc is circular, the interface device can be circular in shape, and so on. The interface device can be made of porous metal such as titanium, or PEEK material (Polyetheretherketone), which is a semi-crystalline organic thermoplastic polymer, or any other suitable biocompatible materials. In some preferred embodiments, the porosity of the material of the interface device can substantially match that of the artificial disc. In some other instances, the porosities of the interface device and the disc can be different. In some preferred instances the interface device and the artificial disc are made of the same material such as porous titanium, for example. In some embodiments, the materials can be different, e.g., the disc is made of titanium and the interface device is made of PEEK polymer. The interface device can also be treated with a biocompatible material such as hydroxyapatite (HA) for improved bone growth to the implant devices.

The interface device of the present invention can be fabricated using three-dimensional ("3D") printing technology, producing it directly from digital descriptions that include output of any software capable of generating a 3D digital model. One example of such software is Computer-Aided Design (CAD) software, which can be implemented on one or more computing devices. Some embodiments of the disclosed device and method will be better understood by reference to the following comments concerning these computing devices.

Figure 3:
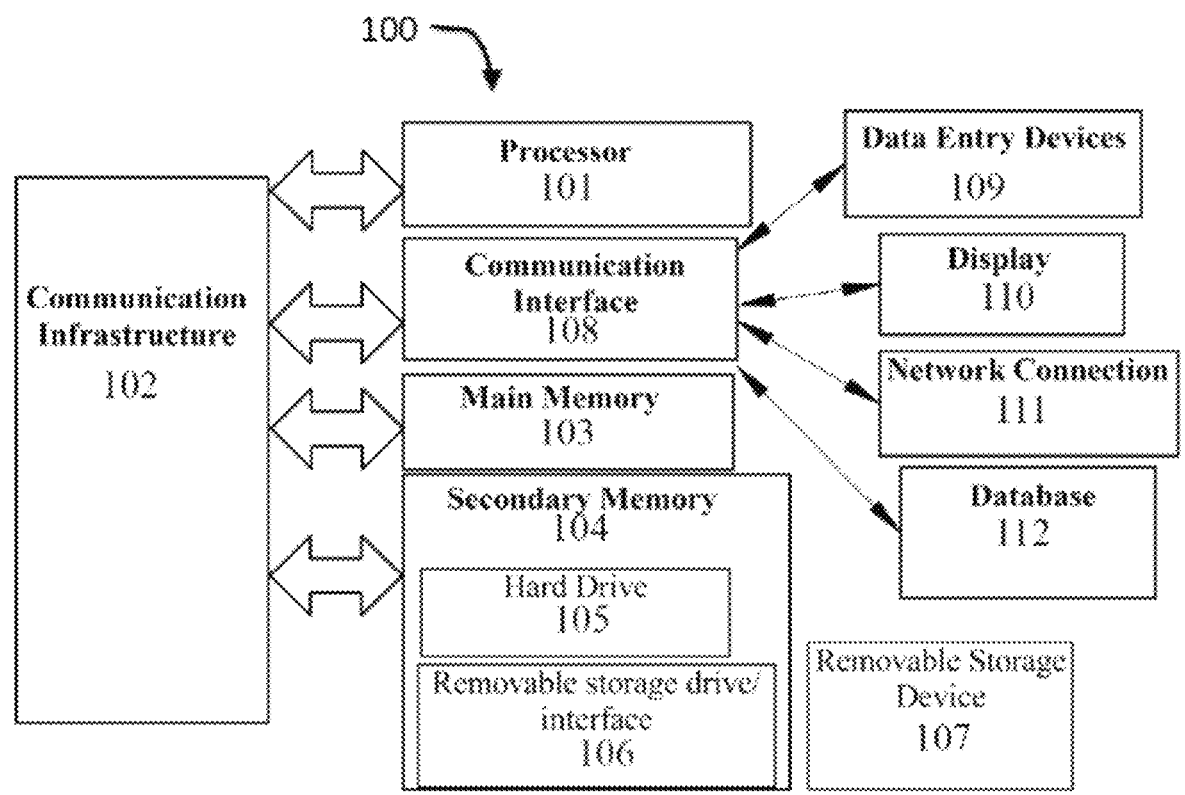
FIG. 3 is a block diagram depicting an example of a computing device as described herein.

A "computing device" 100 may be defined as including personal computers, laptops, tablets, smart phones, and any other computing device capable of supporting an application as described herein. The system and method disclosed herein will be better understood in light of the following observations concerning the computing devices that support the disclosed application, and concerning the nature of web applications in general. An exemplary computing device is illustrated by FIG. 3. The processor 101 may be a special purpose or a general-purpose processor device. As will be appreciated by persons skilled in the relevant art, the processor device 101 may also be a single processor in a multi-core/multiprocessor system, such system operating alone, or in a cluster of computing devices operating in a cluster or server farm. The processor 101 is connected to a communication infrastructure 102, for example, a bus, message queue, network, or multi-core message-passing scheme.

The computing device also includes a main memory 103, such as random access memory (RAM), and may also include a secondary memory 104. Secondary memory 104 may include, for example, a hard disk drive 105, a removable storage drive or interface 106, connected to a removable storage unit 107, or other similar means. As will be appreciated by persons skilled in the relevant art, a removable storage unit 107 includes a computer usable storage medium having stored therein computer software and/or data. Examples of additional means creating secondary memory 104 may include a program cartridge and cartridge interface (such as that found in video game devices), a removable memory chip (such as an EPROM, or PROM) and associated socket, and other removable storage units 107 and interfaces 106 which allow software and data to be transferred from the removable storage unit 107 to the computer system. In some embodiments, to "maintain" data in the memory of a computing device means to store that data in that memory in a form convenient for retrieval as required by the algorithm at issue, and to retrieve, update, or delete the data as needed.

The computing device may also include a communications interface 108. The communications interface 108 allows software and data to be transferred between the computing device and external devices. The communications interface 108 may include a modem, a network interface (such as an Ethernet card), a communications port, a PCMCIA slot and card, or other means to couple the computing device to external devices. Software and data transferred via the communications interface 108 may be in the form of signals, which may be electronic, electromagnetic, optical, or other signals capable of being received by the communications interface 108. These signals may be provided to the communications interface 108 via wire or cable, fiber optics, a phone line, a cellular phone link, and radio frequency link or other communications channels. Other devices may be coupled to the computing device 100 via the communications interface 108. In some embodiments, a device or component is "coupled" to a computing device 100 if it is so related to that device that the product or means and the device may be operated together as one machine. In particular, a piece of electronic equipment is coupled to a computing device if it is incorporated in the computing device (e.g. a built-in camera on a smart phone), attached to the device by wires capable of propagating signals between the equipment and the device (e.g. a mouse connected to a personal computer by means of a wire plugged into one of the computer's ports), tethered to the device by wireless technology that replaces the ability of wires to propagate signals (e.g. a wireless BLUETOOTH® headset for a mobile phone), or related to the computing device by shared membership in some network consisting of wireless and wired connections between multiple machines (e.g. a printer in an office that prints documents to computers belonging to that office, no matter where they are, so long as they and the printer can connect to the internet). A computing device 100 may be coupled to a second computing device (not shown); for instance, a server may be coupled to a client device, as described below in greater detail.

The communications interface in the system embodiments discussed herein facilitates the coupling of the computing device with data entry devices 109, the device's display 110, and network connections, whether wired or wireless 111. In some embodiments, "data entry devices" 109 are any equipment coupled to a computing device that may be used to enter data into that device. This definition includes, without limitation, keyboards, computer mice, touchscreens, digital cameras, digital video cameras, wireless antennas, Global Positioning System devices, audio input and output devices, gyroscopic orientation sensors, proximity sensors, compasses, scanners, specialized reading devices such as fingerprint or retinal scanners, and any hardware device capable of sensing electromagnetic radiation, electromagnetic fields, gravitational force, electromagnetic force, temperature, vibration, or pressure. A computing device's "manual data entry devices" is the set of all data entry devices coupled to the computing device that permit the user to enter data into the computing device using manual manipulation. Manual entry devices include without limitation keyboards, keypads, touchscreens, track-pads, computer mice, buttons, and other similar components. A computing device may also possess a navigation facility. The computing device's "navigation facility" may be any facility coupled to the computing device that enables the device accurately to calculate the device's location on the surface of the Earth. Navigation facilities can include a receiver configured to communicate with the Global Positioning System or with similar satellite networks, as well as any other system that mobile phones or other devices use to ascertain their location, for example by communicating with cell towers. In some embodiments, a computing device's "display" 109 is a device coupled to the computing device, by means of which the computing device can display images. Display include without limitation monitors, screens, television devices, and projectors.

Computer programs (also called computer control logic) are stored in main memory 103 and/or secondary memory 104. Computer programs may also be received via the communications interface 108. Such computer programs, when executed, enable the processor device 101 to implement the system embodiments discussed below. Accordingly, such computer programs represent controllers of the system. Where embodiments are implemented using software, the software may be stored in a computer program product and loaded into the computing device using a removable storage drive or interface 106, a hard disk drive 105, or a communications interface 108.

Computer program code for carrying out operations of the present invention may be written in an object oriented programming language such as, but not limited to, Java, Smalltalk or C++. However, the computer program code for carrying out operations of the present invention may also be written in conventional procedural programming languages such as the "C" programming language. Computer readable program instructions for carrying out operations of the present invention may also be assembler instructions, instruction-set-architecture (ISA) instructions, machine instructions, machine dependent instructions, microcode, firmware instructions, state-setting data, or either source code or object code written in any combination of one or more programming languages described above. In some instances, the computer readable program can be executed in the reverse order, depending upon the functionality involved. It will also be noted that each block of the flowchart illustrations, and combinations of blocks in the flowchart illustrations, can be implement by special purpose hardware-based systems that perform the specified functions or acts or carry out combinations of special purpose hardware and computer instructions.

The computing device may also store data in database 112 accessible to the device. A database 112 is any structured collection of data. As used herein, databases can include "NoSQL" data stores, which store data in a few key-value structures such as arrays for rapid retrieval using a known set of keys (e.g. array indices). Another possibility is a relational database, which can divide the data stored into fields representing useful categories of data. As a result, a stored data record can be quickly retrieved using any known portion of the data that has been stored in that record by searching within that known datum's category within the database 112, and can be accessed by more complex queries, using languages such as Structured Query Language, which retrieve data based on limiting values passed as parameters and relationships between the data being retrieved. More specialized queries, such as image matching queries, may also be used to search some databases. A database can be created in any digital memory.

Persons skilled in the relevant art will also be aware that while any computing device must necessarily include facilities to perform the functions of a processor 101, a communication infrastructure 102, at least a main memory 103, and usually a communications interface 108, not all devices will necessarily house these facilities separately. For instance, in some forms of computing devices as defined above, processing 101 and memory 103 could be distributed through the same hardware device, as in a neural net, and thus the communications infrastructure 102 could be a property of the configuration of that particular hardware device. Many devices do practice a physical division of tasks as set forth above, however, and practitioners skilled in the art will understand the conceptual separation of tasks as applicable even where physical components are merged.

Figure 4:
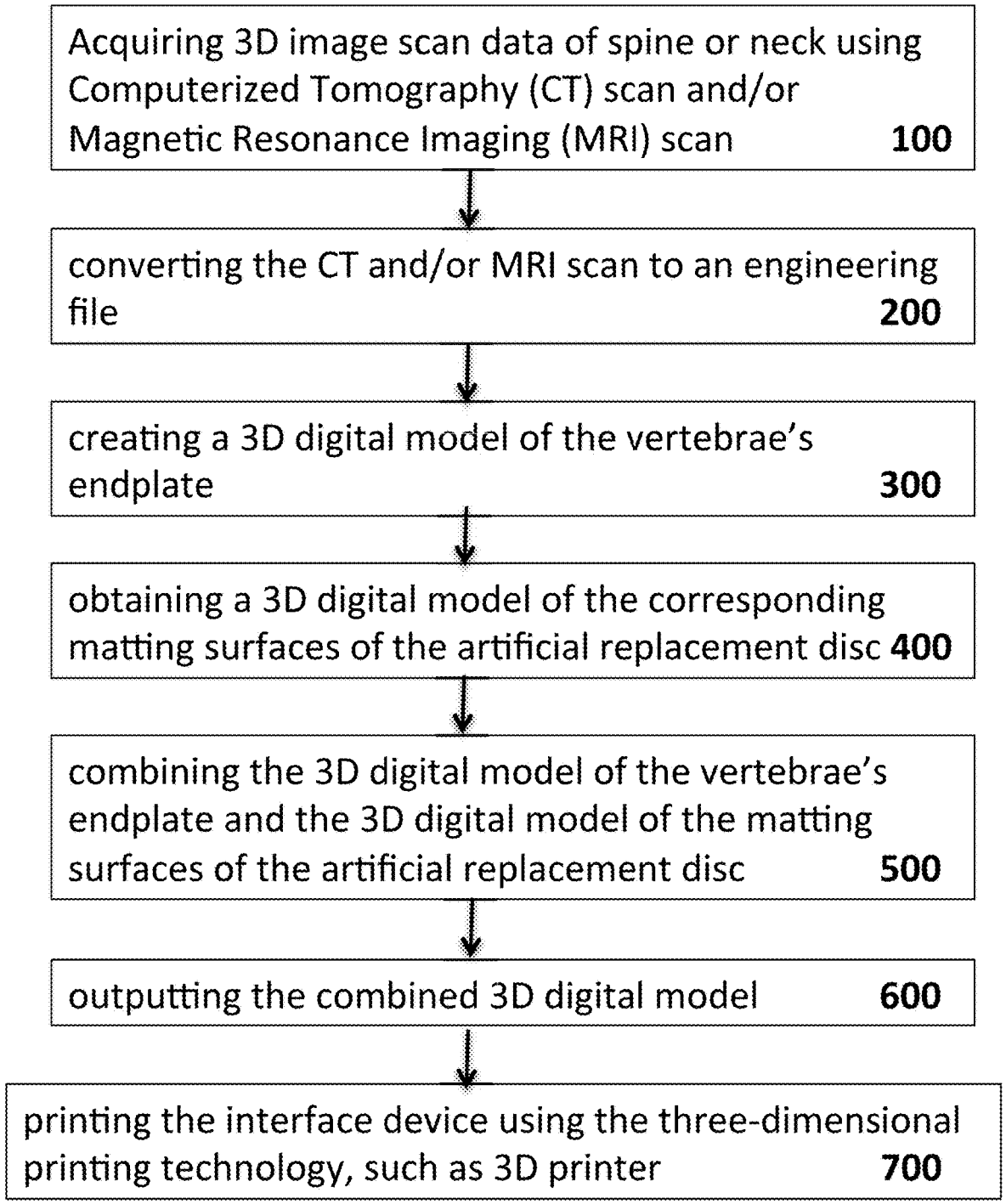
FIG. 4 is a schematic flowchart illustrating the steps of a method for manufacturing an artificial disc interface device in accordance with the embodiments of the present invention.

As illustrated in FIG. 4, the method of fabricating the interface device of the present disclosure includes acquiring 3D image scan data of spine or neck using Computerized Tomography (CT) scan and/or Magnetic Resonance Imaging (MRI) (step 100), converting the CT and/or MM scan to an engineering file (200), creating a 3D digital model of the vertebrae's endplate (300) using a commercially-available software such as Solidworks CAD, for example, obtaining a 3D digital model of the corresponding mating surface of the artificial replacement disc (400), combining the 3D digital model of the vertebrae's endplate and the 3D digital model of the mating surfaces of the artificial replacement disc (500), outputting the combined 3D digital model (600) and printing the interface device (700) using the three-dimensional printing technology, such as 3D printer. According to some embodiments of the present invention, a 3D digital model of the surface morphology of the commercially available replacement discs can be stored and retrieved from the database maintained locally or remotely on the server (such as database 112 of FIG. 3).

It can be appreciated by a person skilled in the art that this process described above can be also applied in the same manner for 3D printing of the artificial replacement disc as one integral part, such that the top and/or bottom surfaces of the disc conform to the corresponding mating surfaces of the corresponding vertebrae's endplates, as discussed in more detail in reference to FIGS. 6-17 below.

Figure 5:
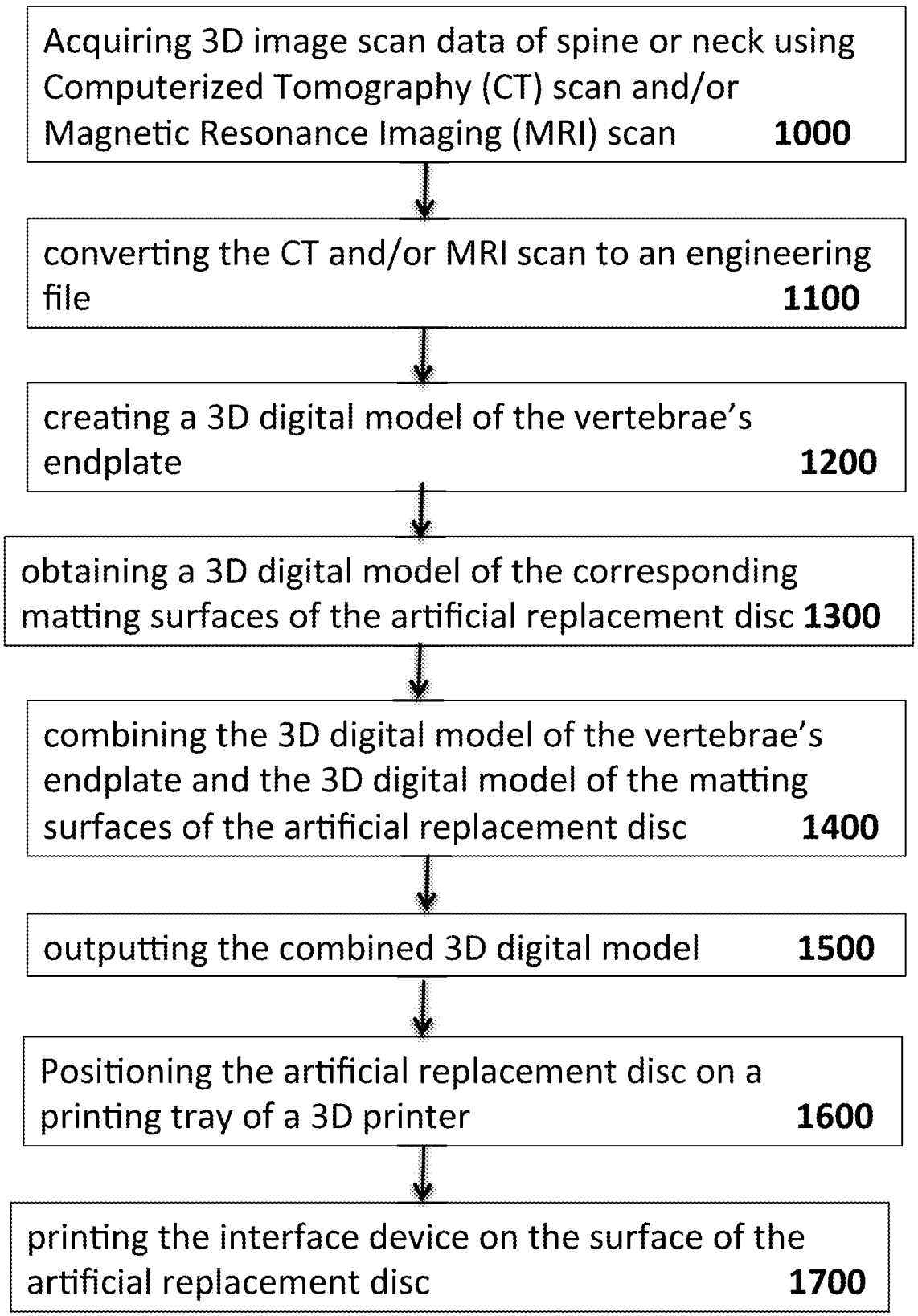
FIG. 5 is a schematic flowchart illustrating the steps of a method for manufacturing an artificial disc interface device in accordance with another embodiment of the present invention.

In some instances, the interface device can be directly printed on the surface of the artificial disc as illustrated by the method of FIG. 5. The method includes acquiring 3D image scan data of spine or neck using Computerized Tomography (CT) scan and/or Magnetic Resonance Imaging (MRI) scan (step 1000), converting the CT and/or MM scan to an engineering file (1100), creating a 3D digital model of the vertebrae's endplate (1200), obtaining a 3D digital model of the corresponding matting surfaces of the artificial replacement disc (1300), combining the 3D digital model of the vertebrae's endplate and the 3D digital model of the matting surfaces of the artificial replacement disc (1400), outputting the combined 3D digital model (1500), positioning the artificial replacement disc on a printing tray of a 3D printer (1600), and printing the interface device on the surface of the artificial replacement disc (1700).

In some embodiments of the present invention, a 3D printer can be combined with a 3D scanner for scanning the surface of the artificial replacement disc prior to printing on its surface, thereby gaining accurate data on that surface before the print begins and eliminating a laser line distortion when it hits the object on the 3D printer's printing bed. Alternatively, the disc and the interface device can be two separate parts as described above with reference to FIGS. 2A-2B.

Once fabricated, the interface device can be disposed on top and/or bottom of the artificial disc and used in the artificial disc replacement procedure described in the background section of the present disclosure. The interface device can be permanently attached to the artificial disc using any suitable attaching means such as glue, for example; or it can be detachably attached by way of corresponding protrusions and grooves, such as illustrated in FIG. 2B; or it can be placed on the artificial disc without using any attaching means (i.e., the interface device and artificial disc are being pressed together by force of two vertebrae between which the device and disc are positioned). In some instances, one interface device can be disposed on top of the artificial disc and another interface device can be disposed on the bottom of the artificial disc. It can also be directly printed on the surface of the artificial disc, as discussed above in related to a method illustrated in FIG. 5, forming one integrated part, or it can be comprised of two separate parts.

Below is a more detailed discussion of application of the bio-mechanically compatible 3D-printed intervertebral disc of the present disclosure for solving many problems in the human spine related, but not limited to, intervertebral disc diseases.

Figure 6A:
FIGS. 6A, 6B, and 6C illustrate a conventional process of producing spinal implants.
Figure 6B:
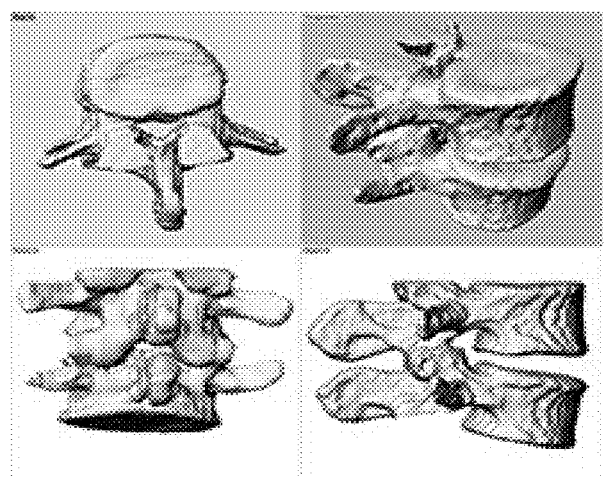
Figure 6C:
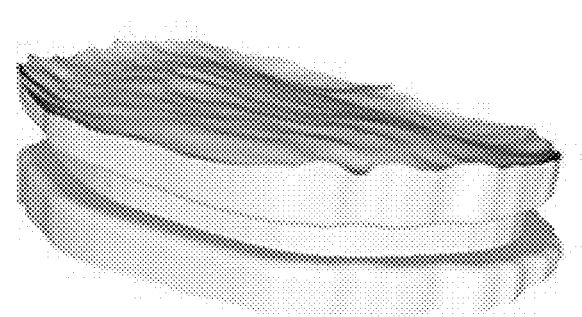

The practical application and combination of medical imaging, as shown in FIG. 6A, 3D analysis & software conversion to a 3D engineering file (FIG. 6B), surgery preparation software and 3D printing techniques (FIG. 6C) to produce spinal implants (both fusion implants and functional, moveable artificial intervertebral discs) which are custom shaped per patient, per level (any level of the human spine).

Figure 7:
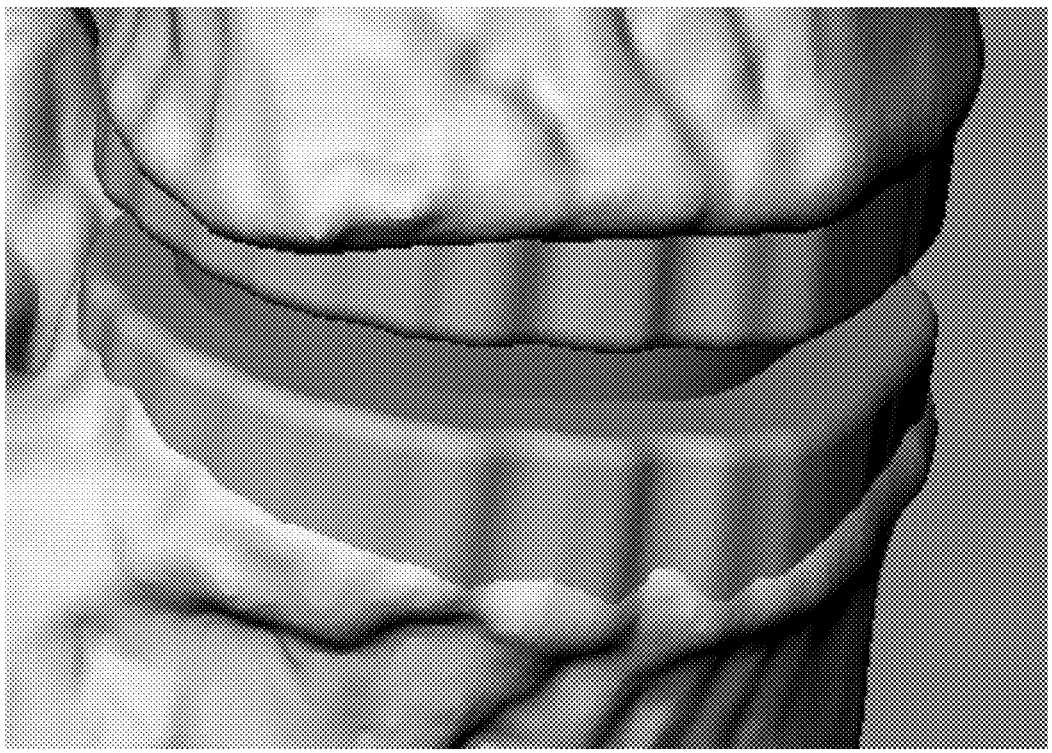
FIG. 7 is an illustration of a 3D-printed artificial endplates.

These are 3D printed artificial endplates made of any biocompatible material to match the natural shape of the patient's bone structure, as illustrated in FIG. 7. The final implant also matches and maintains the proper spinal lordosis. The endplate surfaces match the bone surfaces and extend to the perimeter of the vertebral bodies for optimal homogenous load carrying and distribution, support, and marriage to the bone, which will make subsidence of the implant impossible and faster recovery of the patient. The angle of the implants can be infinitely adjusted in the design, to match the proper bone angles and thus spinal lordosis for optimal sagittal balance. An additional benefit of covering as much as possible of the bone's endplates is to prevent heterotopic ossification (HO).

Figure 8:
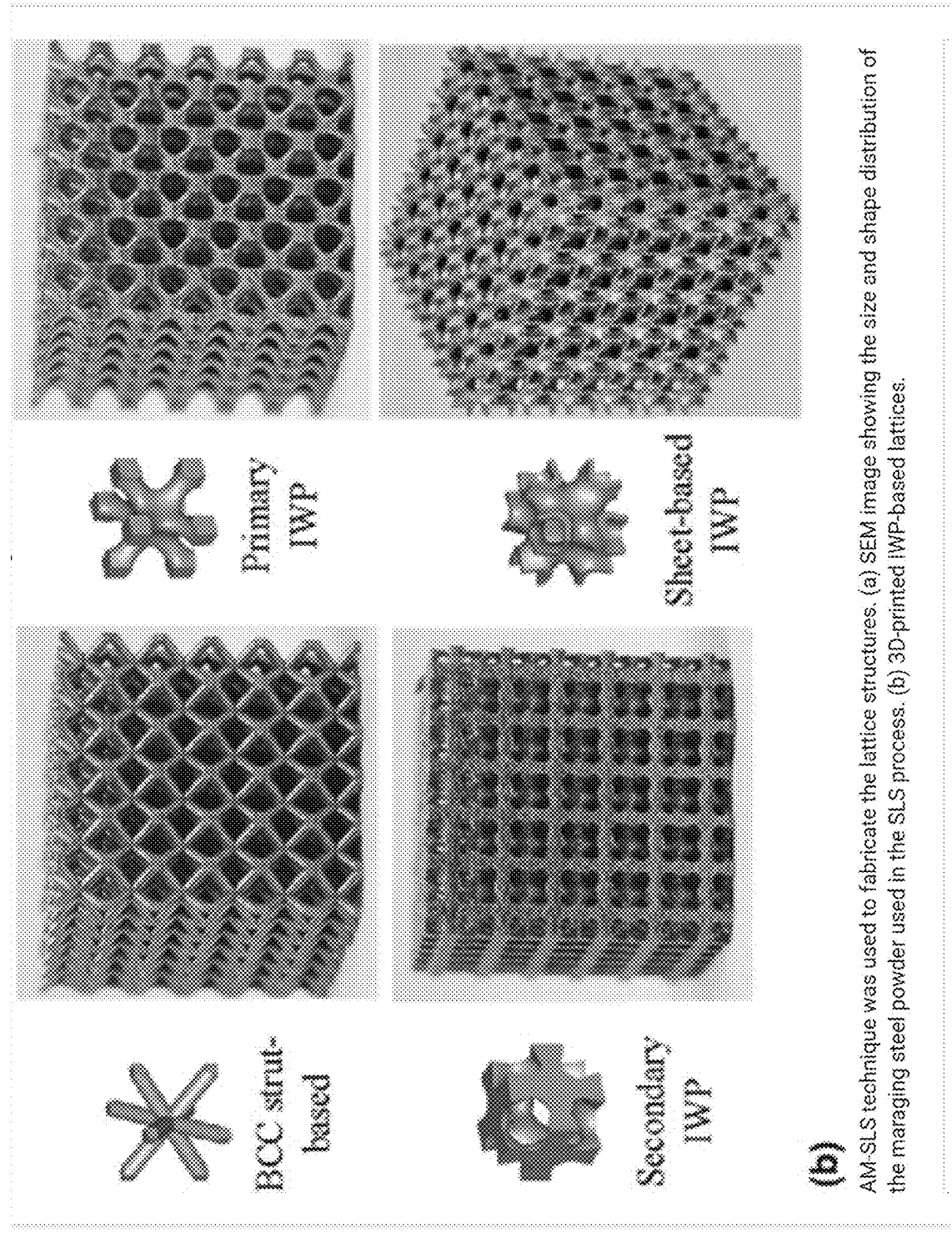
FIG. 8 illustrates the lattice structures using 3-D printing methods.

Together with the matching of the implant endplates' shape to the shape of the bone endplates, the special bone penetrating friction details on the implant's endplate surfaces provide additional grip and adhesion to the bone, and a faster strong bond to the bone. One benefit of 3d printing the endplate material is that open or lattice structures can easily be added where desired, to control the bone in-growth to the marrying vertebral surfaces, as shown in FIG. 8. Another benefit of 3D printing the endplate material is that the printed surface is relatively rough, which is excellent for bone adhesion.

Figure 9:
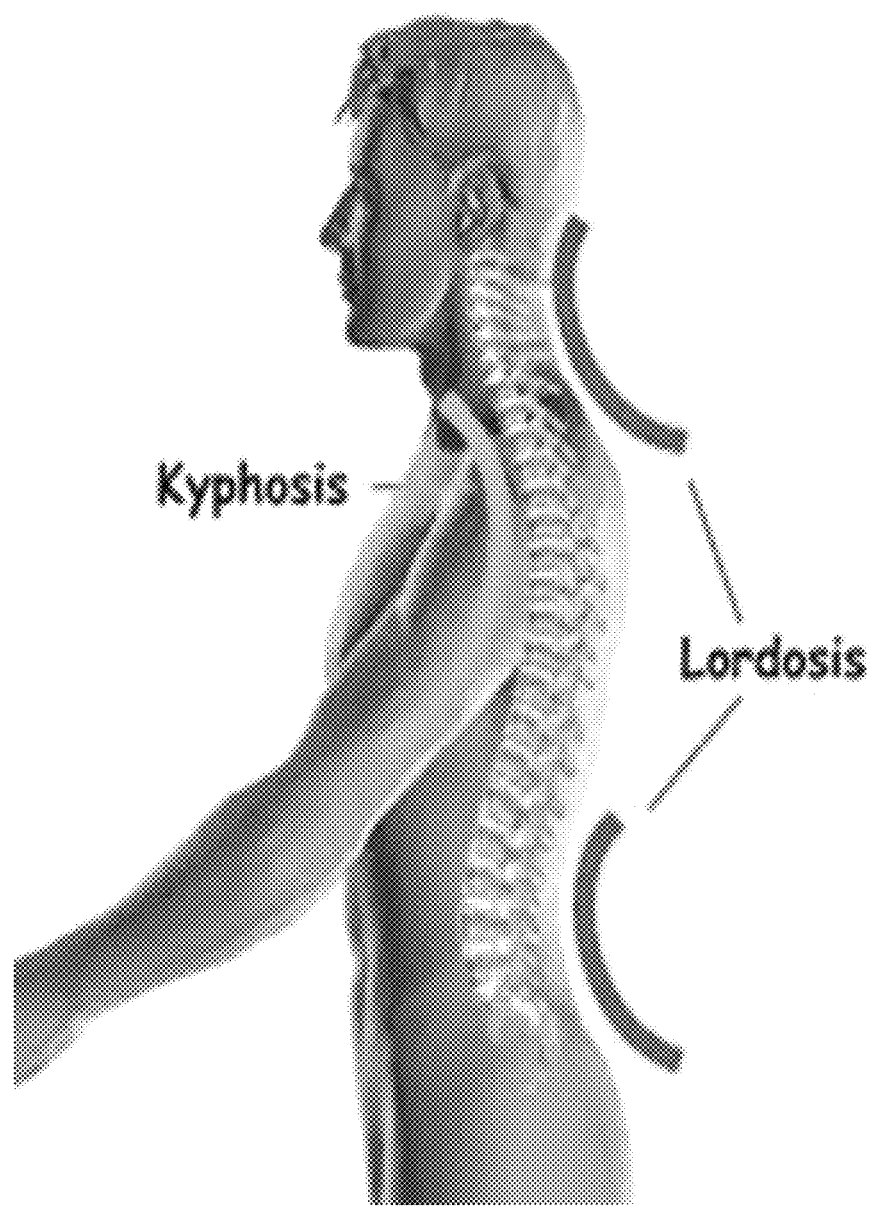
FIG. 9 shows varying angles between the vertebrae bone endplates.

Patients have varying angles between the vertebrae bone endplates, which determines the lordosis and kyphosis in their spines. These angles are specific to each patient and must be respected to maintain optimal sagittal balance and healthy movement and spacing in the facets and between the vertebrae, as shown in FIG. 9.

Current known artificial disc designs are known to fail when the lordosis of the spine is not respected and restored during surgery. This happens—for instance—in cases of hyperlordosis, when there is no availability of fusion cages with a high enough angle to correctly recreate the natural lordosis. The approach of the presently disclosed invention addresses such problems directly and without limits to angle, size, spacing or shape. With this new technology, any natural angle between a pair of vertebrae can be matched, as well as any height, as illustrated in FIG. 10, to maintain the right lordosis, plus fix and potentially correct eventual scoliosis. Especially scoliosis caused by a lateral tilted pelvis (caused by difference of leg lengths i.e.) can be corrected so that the L5 vertebra can be aligned horizontally by adjusting the angle of the misaligned Si (Top level of the Sacrum), to let nature and physiotherapy self-correct the spine above L5 and thus the scoliosis.

Figures 10A, 10B:
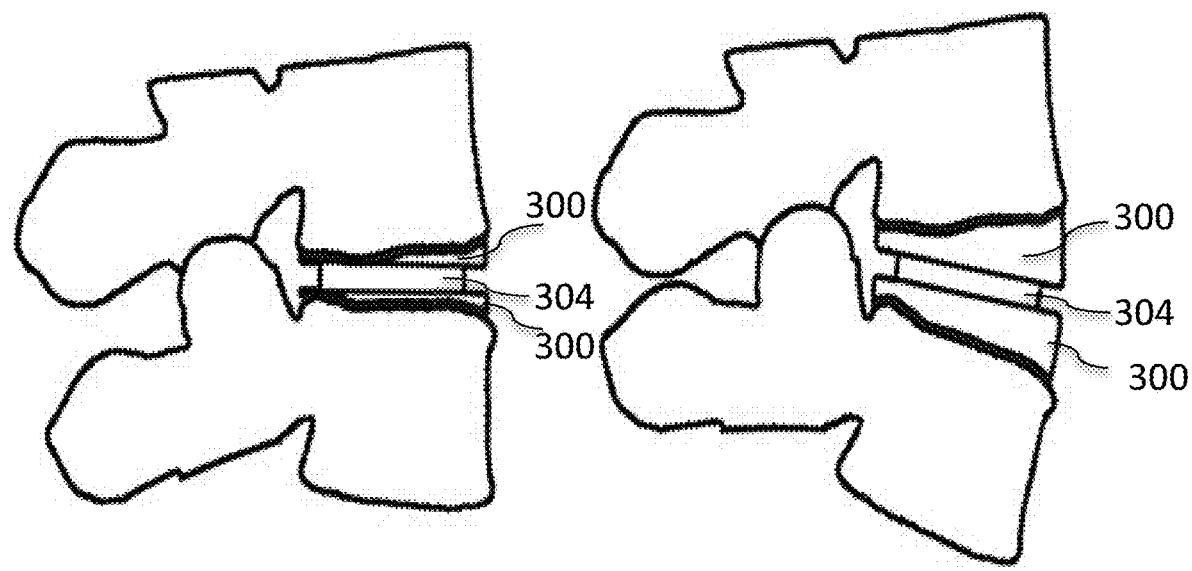
FIGS. 10A-10B is a schematic illustration of the disc in accordance with the embodiments of the present disclosure.
Figure 11A:
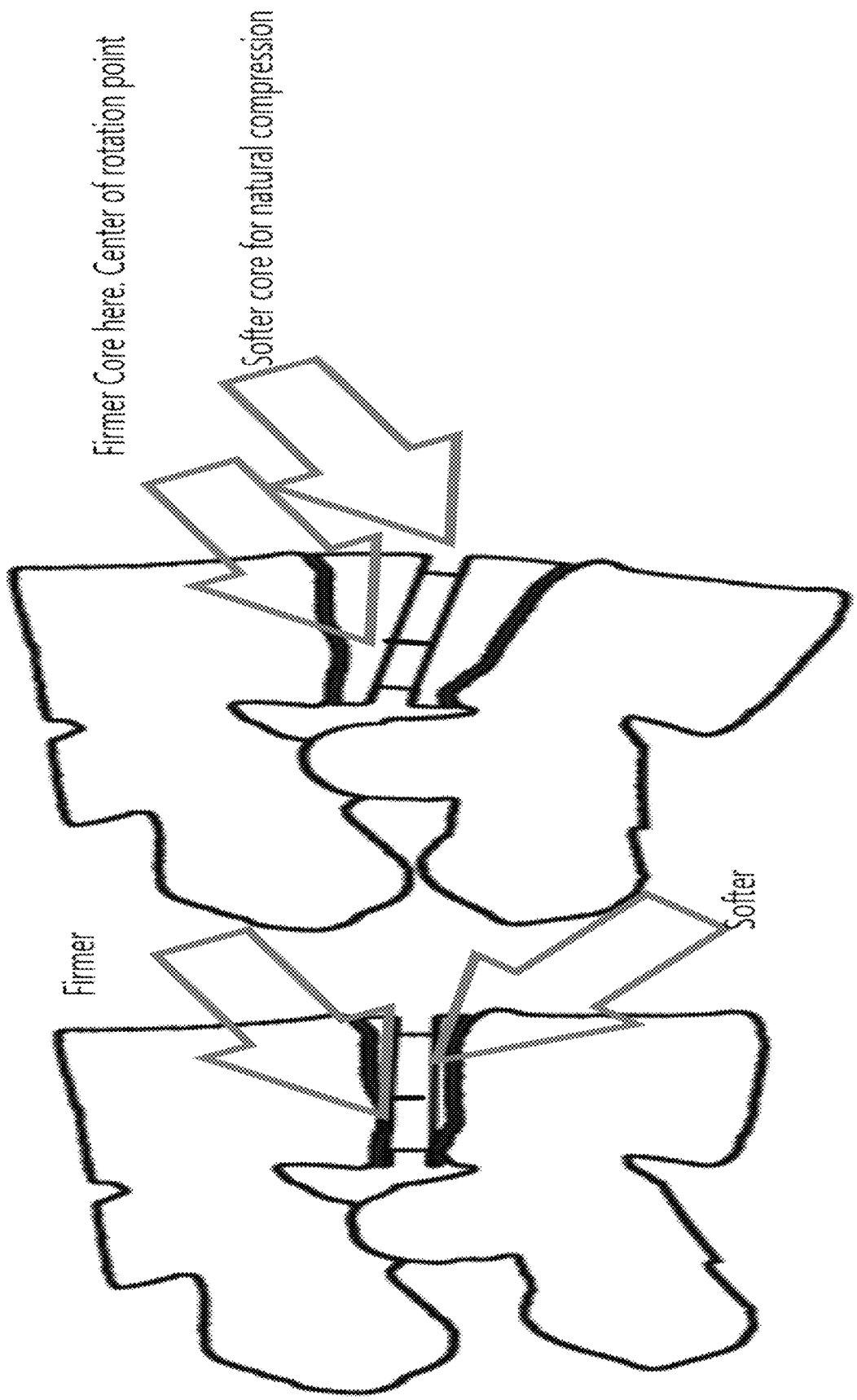
FIG. 11A is a schematic illustration of the disc in accordance with the embodiments of the present disclosure with the core comprised of materials having different stiffness.

The implant of the present disclosure is designed in such a way, that when the spine is in the neutral position (in sagittal balance), the core (304) of the artificial disc is oriented parallel, as shown in FIGS. 10A-10B, and the angle and morphology of the implant's endplates (300) precisely matches the patient's anatomy. This facilitates equal freedom of movement in all directions from the neutral position of the artificial disc. In some instances, the core can be comprised of one biocompatible visco-elastic material, and in some instances, two or more visco-elastic materials having different stiffnesses, as shown in FIG. 11A.

Figure 12:
FIG. 12 illustrates the flaws or imperfections of the prior art artificial discs.

It must be noted that currently known artificial disc implants cannot accommodate the endless variations and often cause metal-to-metal contact points or instability due to their mechanical components getting affected or shifting out of position, as illustrated in FIG. 12.

According to the embodiments of the present invention, the firmer, load bearing section of the core is located closer to the spinal cord, rather than in the center of natural intervertebral disc (like most other implants), to facilitate good angular movement, while minimizing the dynamics in the facet joints. In other instances, the core can be manually shifted to any desired location.

Figure 11B:
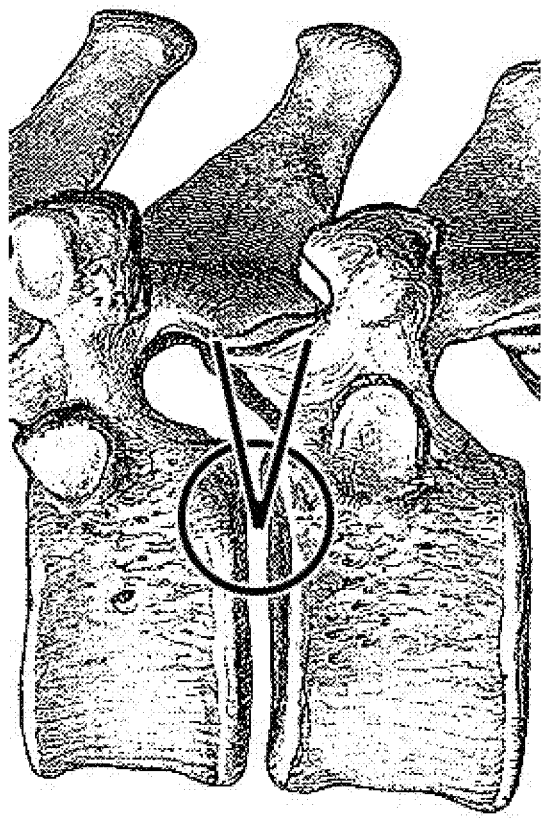
FIG. 11B shows a vertical displacement of the facet joints in a standard disc versus minimal vertical displacement of the facets in a disc having the tougher core closer to the spinal cord in accordance with an embodiment of the present invention.
Figure 11B:
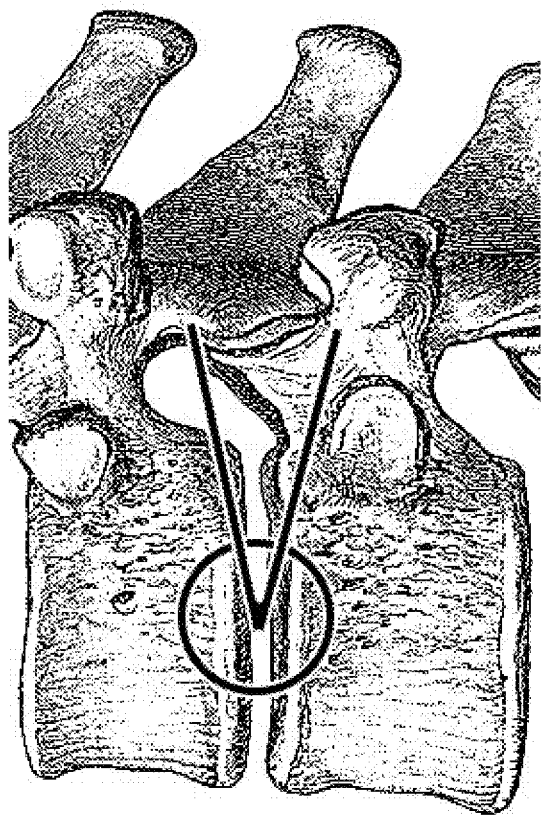

According to some embodiments of the present disclosure, the core has a floating Center Of Rotation (COR). The softer core material is located in the remaining space between the tougher core and the perimeter, which enables easier compression during flexion, extension and lateral bending, so the vertical displacement of the facet joints and the stretching of the Posterior Longitudinal Ligament (PLL) are minimized. The goal of this is to minimize the wear of the facet joints and the stress on them, as shown in FIG. 11B which is a seesaw-like illustration of much vertical displacement of the facet joints in a normal disc, versus minimal vertical displacement of the facets in the case of having the tougher core closer to the spinal cord, in accordance with an embodiment of the present disclosure. Under extension (bending backwards) and flexion (bending forwards), the COR resides inside the flexible core, moving slightly in AP direction. Under lateral bending (sideways), the COR resides inside the flexible core, moving slightly from left to right. Under axial rotation, the COR resides outside the flexible core in the lumbar area, closer to the backside of the spinal cord, as dictated by the shape of the lumbar facet joints, so the core allows lateral shearing to facilitate this. All these movements imitate the behavior of the natural disc.

Figure 13:
FIG. 13 is an illustration of an oversized prior art implant.

Under compression the stiffer section of the core maintains proper disc height and prevents damage to the facet joints and maintains proper neural pathways in the spine. Using proper preoperative medical imaging techniques combined with our 3D printing approach, the surgeon has the ability to infinitely adjust the endplate thickness, size, angle and shape. The goal is to minimize over-distraction (which causes excessive pain) and recovery time. With competitive designs, the surgeon is often forced to place an oversized implant, which adds significant stretching to the tendons and ligaments (beyond their normal maximum range, as shown in FIG. 13), and can cause improper alignments and angles, but also may cause additional compression of adjacent intervertebral discs, causing a poor solution for the patient. With the system of the present invention the surgeon is able to determine the correct height and angles for the patient prior to surgery.

Figure 14B:
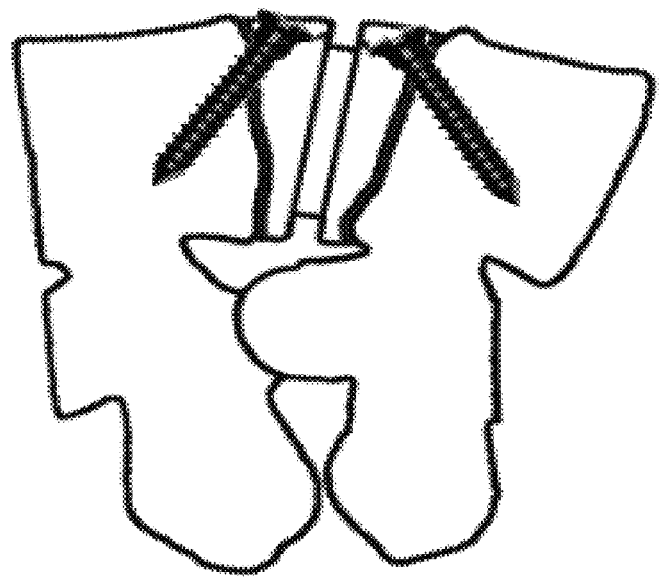
FIGS. 14A and 14B illustrates some alternative embodiments of the present disclosure.
Figure 14A:
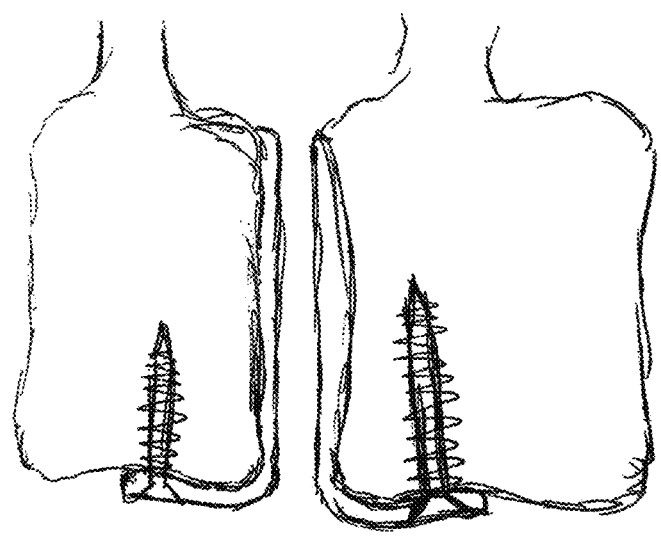

The core can be shifted more anterior or posterior (relative to the endplate surfaces) as desired, prior to 3D printing. The stiffness of the core components can be adjusted in function of the patient's size and weight. When desired, one or more lips, each with one or more screw-holes in them, can be added anywhere on the perimeter of the endplates to mechanically secure the implant with additional screws. This further prevents any possible migration of the implant. (FIG. 14A). In case of the hyperlordosis implants, it is possible to add screw holes in the endplates to prevent implant migration from too high angle differences and resulting AP shearing forces. (FIG. 14B)

For cases of slipping discs, an extra tough core can be created, optionally with extra barriers placed inside the soft core of the implant, to mechanically limit the displacement of the endplates, which can add extra stability to the realigned vertebrae. The use of medical imaging to produce medical 3D printed implants also extends to the creation of other support structures which could be bolted onto the fusion cages (or combine them with the fusion cage as one 3D printed part), to offer much more strength and stability to a fusion of 2 or more vertebrae, if needed, as an alternative to posterior stabilization with screws and rods that damage the soft tissues posterior to the spine.

Figure 15:
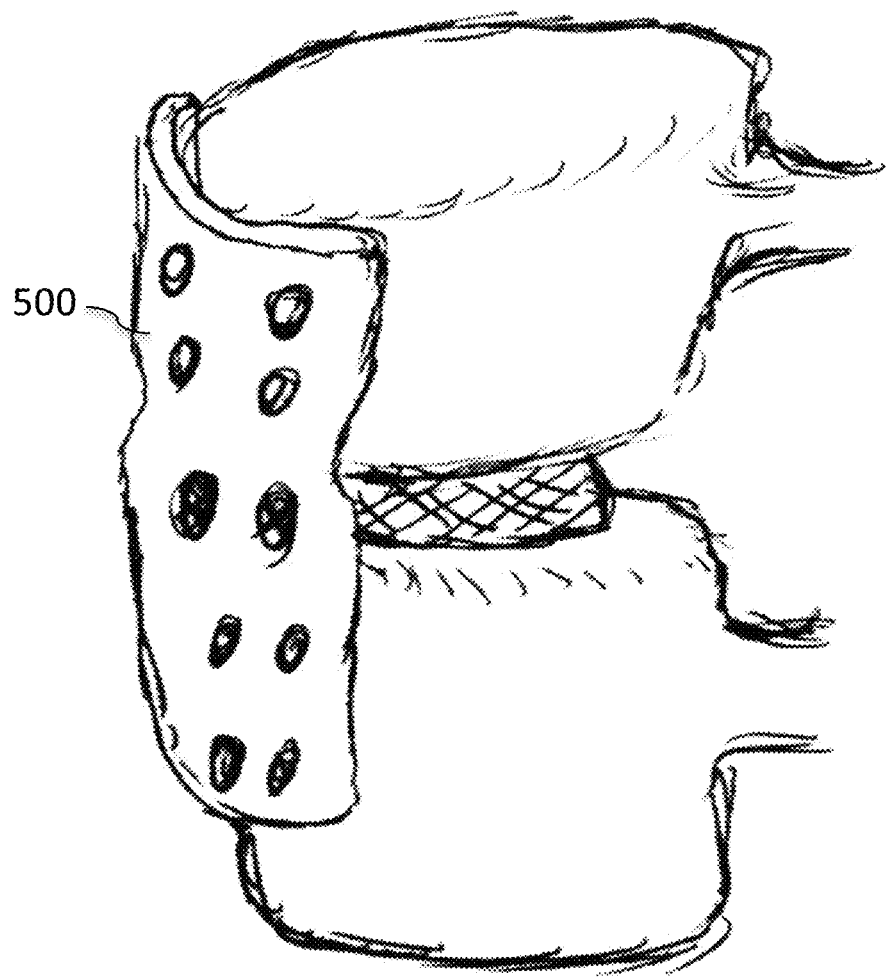
FIG. 15 shows another embodiment of the present disclosure.

This would be plates, which are an offset of the bone surfaces (after realigned into the proper position in the 3D medical software), to form a plate of an infinitely adjustable desired thickness, filled with holes to first mount the plate onto the placed fusion cage, and secondly to additionally screw the plate to the rest of the outer surface of the vertebrae (above and below the fusion cage). Such an interlocking plate may span over more than 2 vertebrae, if needed. The plate 500 follows the curvature of the bone, thus has additional strength due to the natural cylindrical curvature, as illustrated in FIG. 15.

The spine will effectively be upgraded because of an implant like this, since it will have the same motion as the natural intervertebral disc, but it will be stronger and more durable and not subject to dehydration by vertical static pressure (working while standing or sitting still a lot). Where the central part of the vertebral superior and inferior bone endplates could normally collapse in certain high shock load/accident situations (falling on one's behind), the presence of this artificial disc would prevent bone collapse, as the stiff titanium implant endplates would distribute that load more to the outer edges of the bone, which are the strongest part of the vertebral main bodies.

Figure 16:
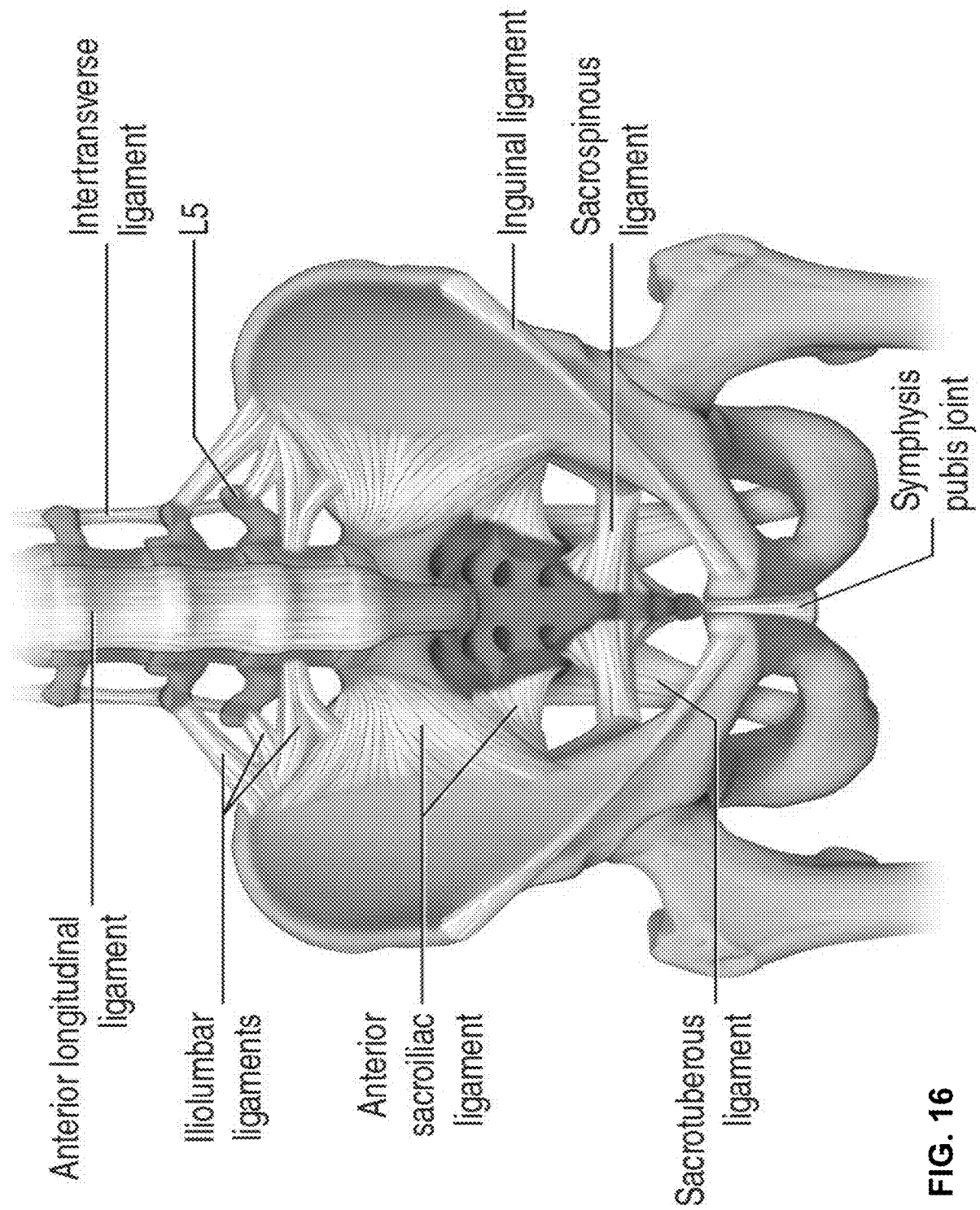
FIG. 16 is a schematic diagram illustrating the support structures of the ligaments that restrict rotation of the L4 and L5 vertebrae.

As illustrated in FIG. 16, one can see the support structures of the ligaments that specifically restrict rotation of the L4 and L5 vertebrae, but allow flexion and extension. To allow rotation about the vertical axis, the vertebrae need to undergo lateral translation, which in turn needs the intervertebral disc to allow lateral shearing. The implant of the present disclosure is designed to accommodate any of these movements.

Figure 17:
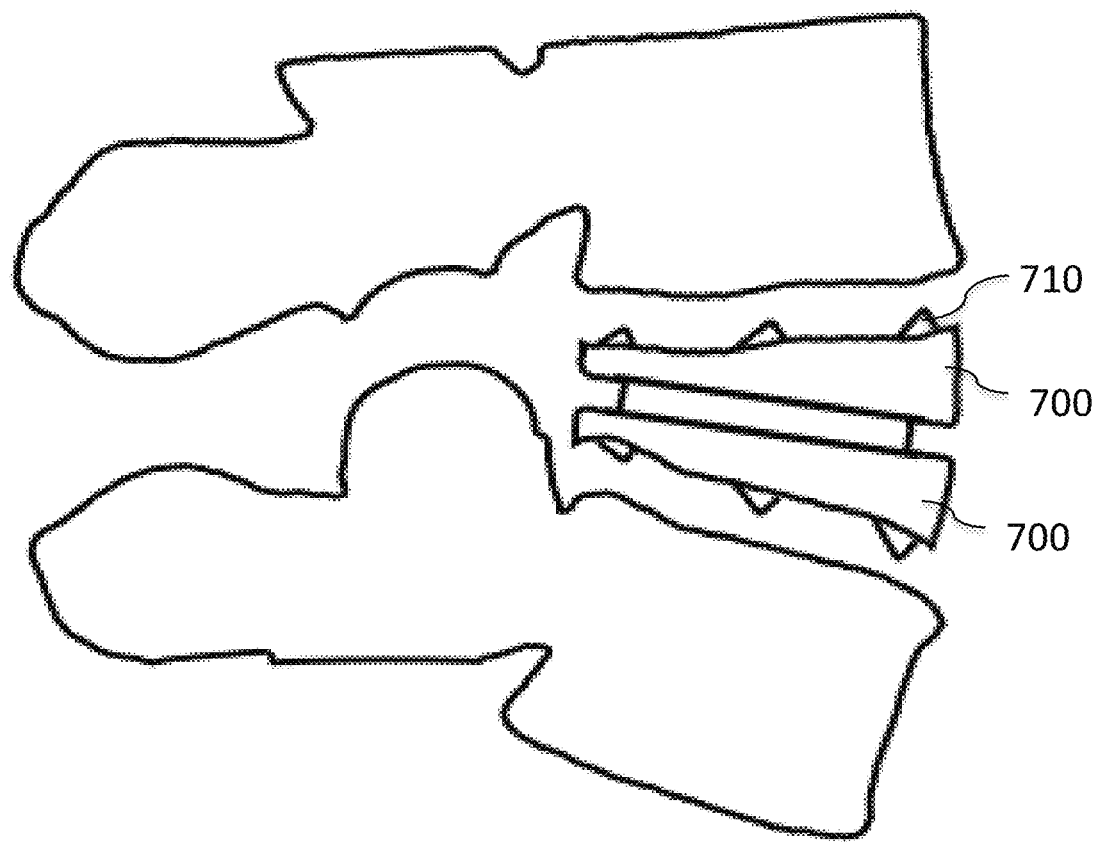
FIG. 17 shows the implant with protrusions in accordance with another embodiment of the present disclosure.

Optional protrusion shapes 710 (any shape, like spikes, teeth, keels, lattice pyramids, and others) can be added to the outer surface of the implant endplates 700 to add more grip on the mating bone surface against migration, as shown in FIG. 17.

Figure 18:
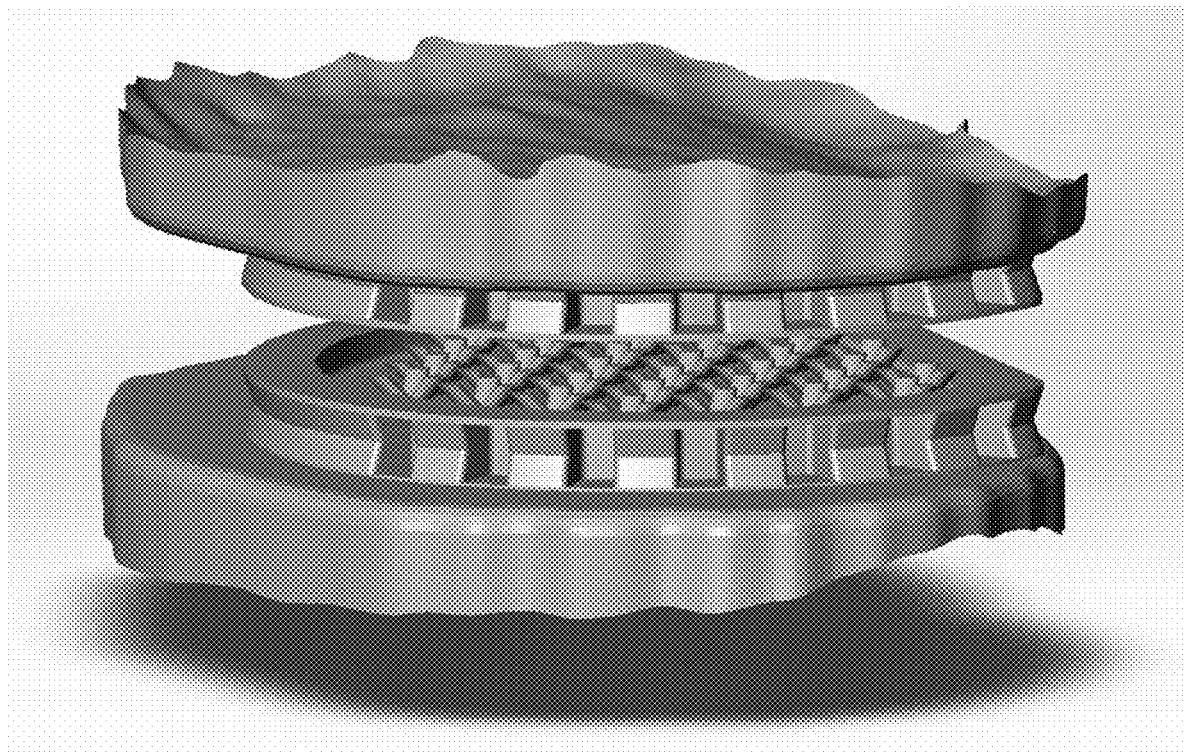
FIG. 18 is a schematic illustration of the disc in accordance with the embodiments of the present disclosure showing endplates with slots for gripping.
Figure 19:
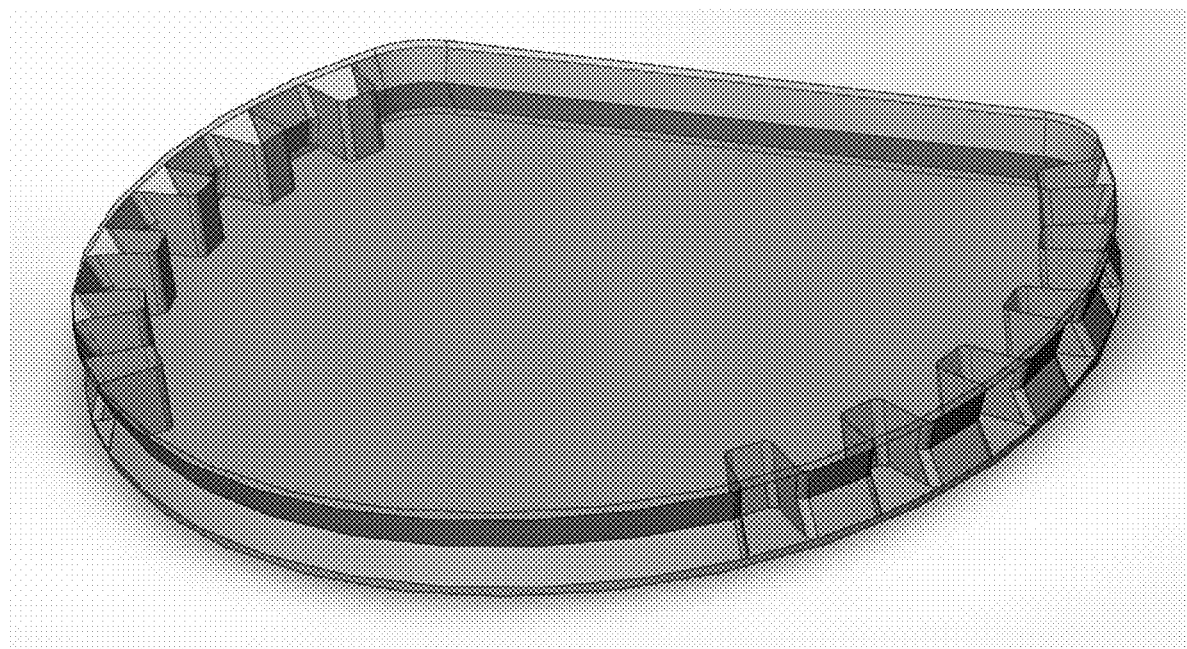
FIGS. 19-20 shows a portion of the endplate having a plurality of slots for gripping.
Figure 20:
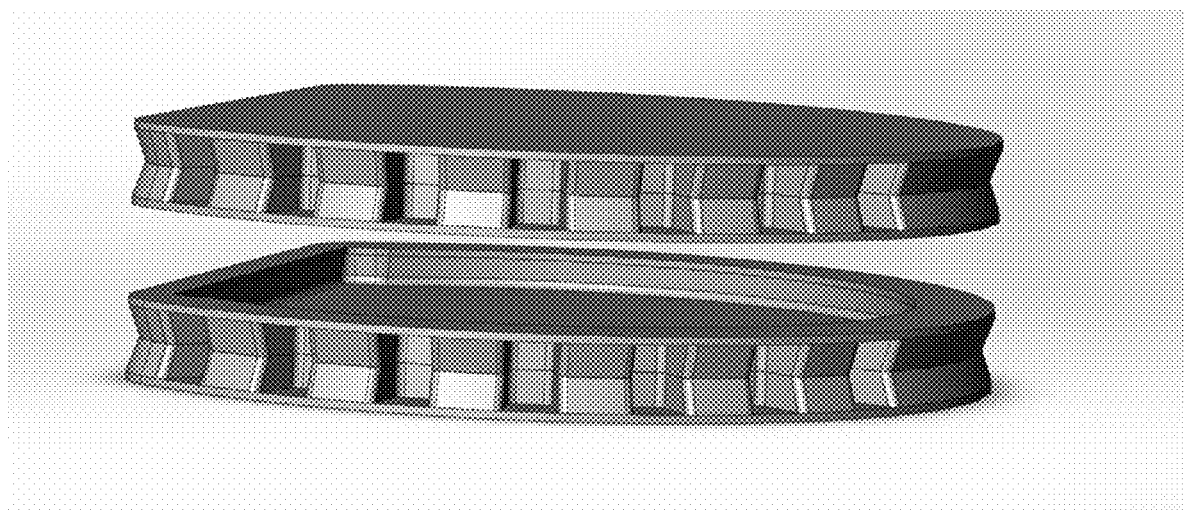
Figure 21A:
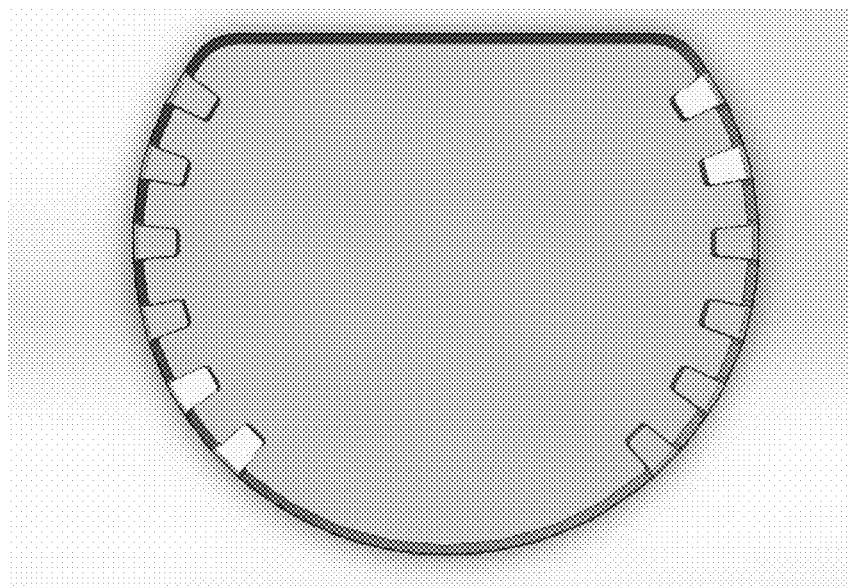
FIGS. 21A-21C show a multi-prong gripping configuration.
Figure 21B:
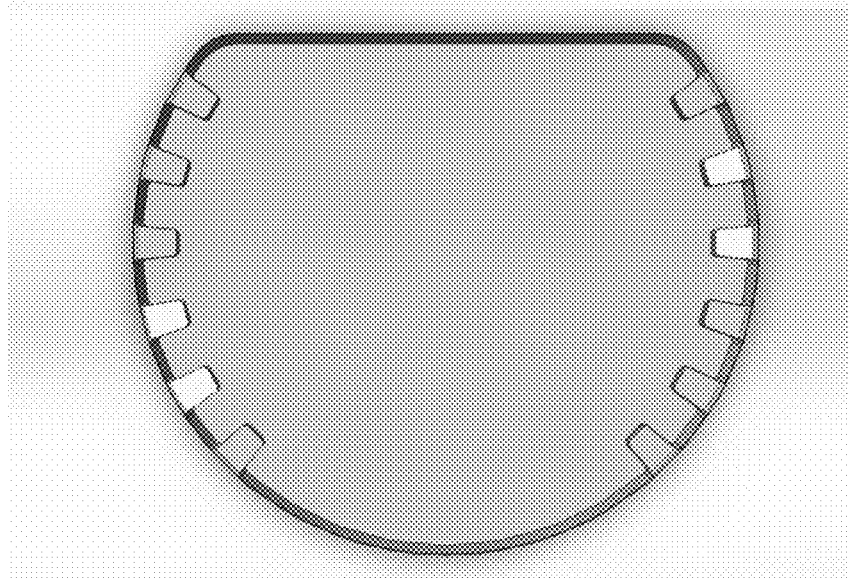
Figure 21C:
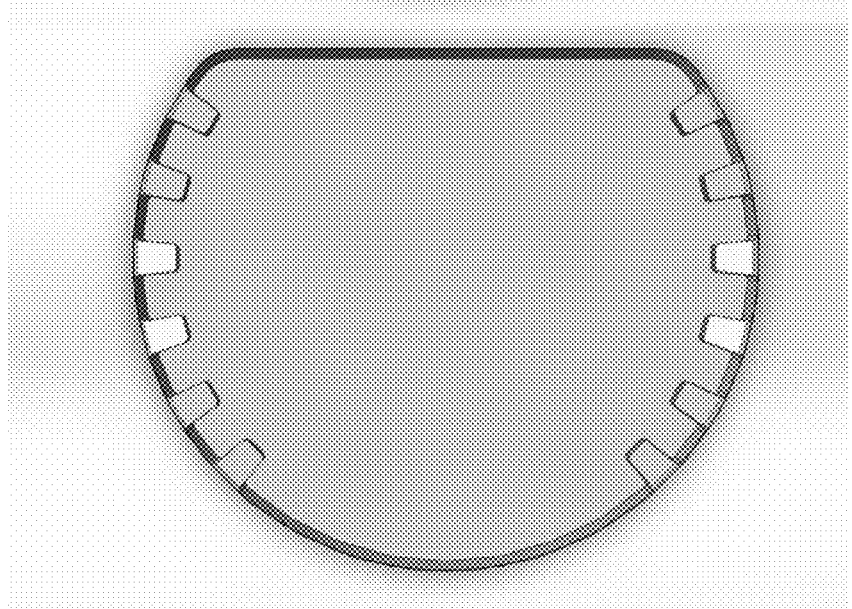
Figure 22A:
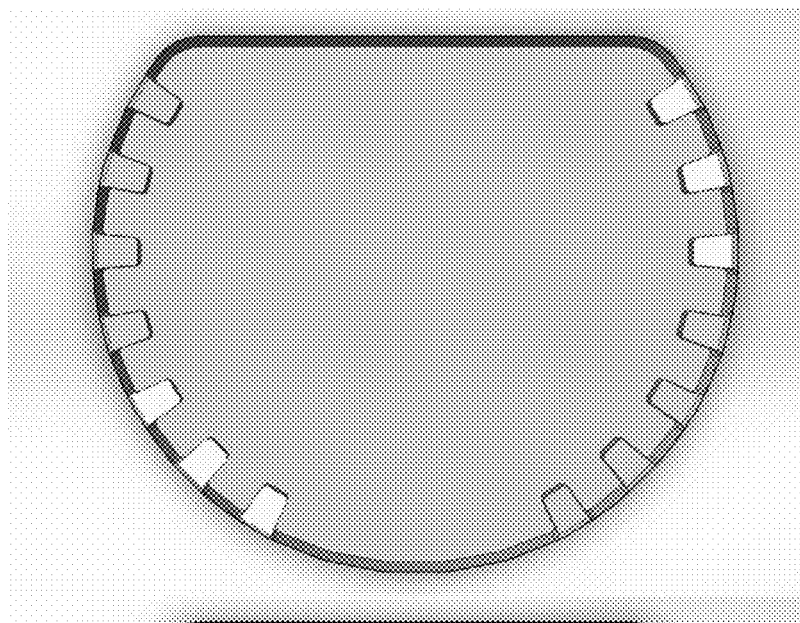
FIGS. 22A-22C show another multi-prong gripping configuration.
Figure 22B:
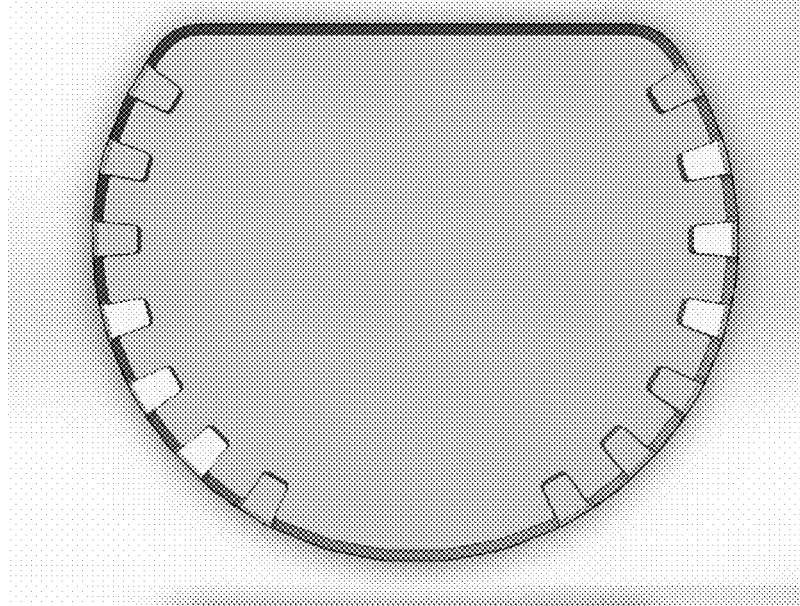
Figure 22C:
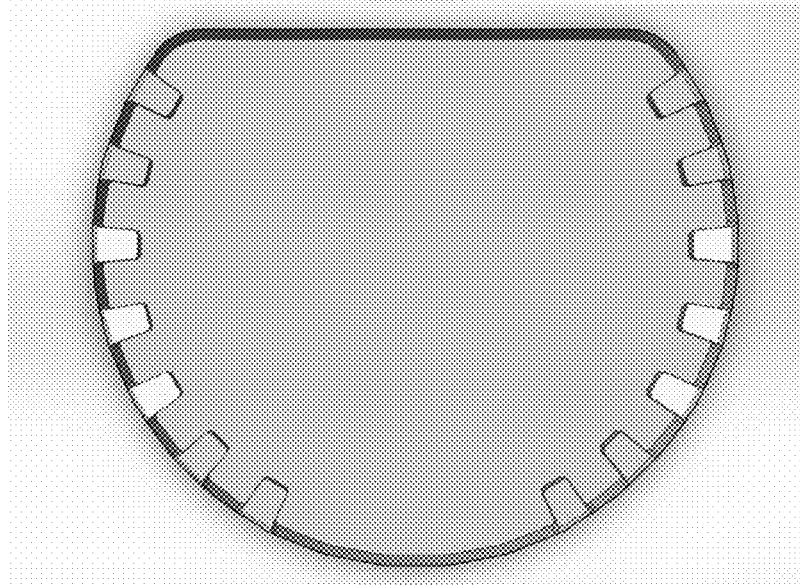

According to another embodiment of the present disclosure, the endplates of the artificial disc implant can have a gripping structure for ease of gripping the disc with various gripping tools. As illustrated in FIGS. 18-20, a top endplate 800 includes a first portion 810 a having a surface matching the morphology of the corresponding bone endplate and a second portion 810 b having a plurality of gripping slots 950 protruding inwardly for receiving a gripping tool. Likewise, a bottom endplate 900 includes a first portion 910 a having a surface matching morphology of a corresponding bone endplate and a second portion 910 b with a plurality of gripping slots 950 protruding inwardly for receiving a gripping tool. It will be appreciated by a person skilled in the art that a first and second portions of the top and bottom endplates can be formed using 3D printing methods as one integral part. In some instances, the top and bottom endplates can be formed by attaching a first portion and a second portion as two separate parts using commercially available attaching means such as glue or adhesive, for example. The gripping tool can grip the disc at different slot positions as illustrated in FIGS. 21A-21C, thereby allowing to access the disc with the gripping tool at different angles, which makes it easier to place the artificial replacement disc between the bone endplates without damaging other organs such as arteries, for example. With a two-prong gripping tool the disc can be gripped at slots 950 a and 950 c, or 950 a and 950 d, and so on. Likewise, with a four-prong tool, the disc can be clamped at 950 a/950 d and 950 c/950 d slots at various positions on the perimeter of a second portion of an endplate. With a six-prong gripping tool, the endplate can be clamped at three slots from each side of a second portion of an endplate, as illustrated on FIGS. 22A-22C.

Figure 23:
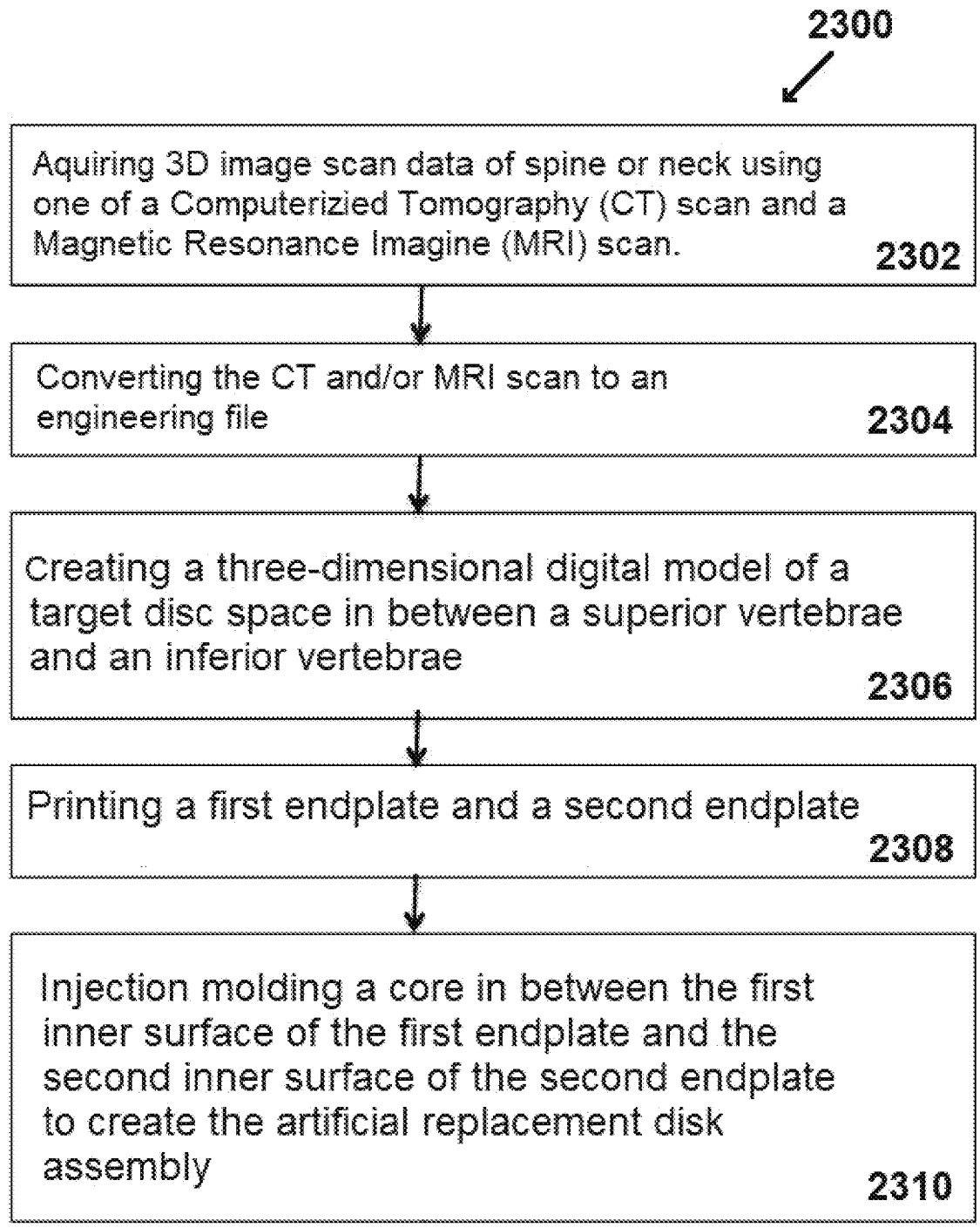
FIG. 23 is a schematic flowchart illustrating the steps of a method for manufacturing an artificial replacement disk assembly in accordance with the embodiments of the present invention.

Now referring to FIG. 23, one exemplary method 2300 of fabricating an artificial replacement disk comprises the steps of acquiring three-dimensional image scan data of spine or neck using at least one of computerized tomography (CT) scan and magnetic resonance imaging (MRI) 2302, converting the CT and/or MRI scan to an engineering file 2304, creating a three-dimensional digital model of a target disc space in between a superior vertebrae and an inferior vertebrae 2306, printing a first endplate and a second endplate 2308, and injection molding a core in between the first inner surface and the second inner surface to create the artificial replacement disk assembly 2310.

Figure 24A:
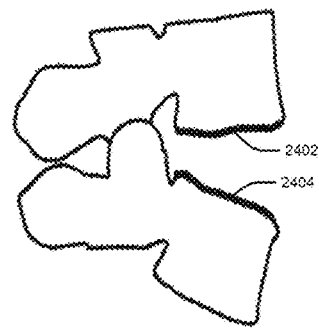
FIGS. 24A-24G depict the steps of method of FIG. 23, in accordance with one embodiment of the present invention.
Figure 24B:
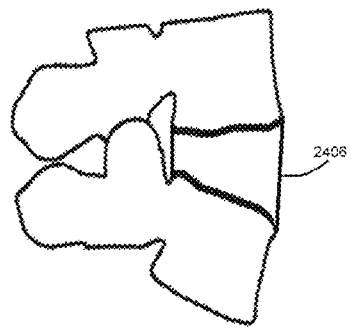
Figure 24C:
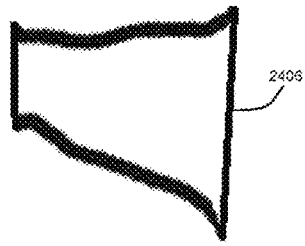

FIGS. 24A-24F depict a cross-sectional view of the steps of the method of FIG. 23. In FIG. 24A, a spine portion is scanned using CT or MRI technologies. The spine portion includes a superior vertebrae 2402 and an inferior vertebrae 2404. The scan data is converted into an engineering file to create a three-dimensional digital model 2406 of a target disc space in between a superior vertebrae and an inferior vertebrae as shown in FIGS. 24B-24C. The digital model 2406 may be created by filling in an area in between the vertebral endplates of the superior and inferior vertebrae, where the top surface of the digital model matches the surface morphology of the superior vertebrae and the bottom surface of the digital model matches the surface morphology of the inferior vertebrae.

Figure 24D:
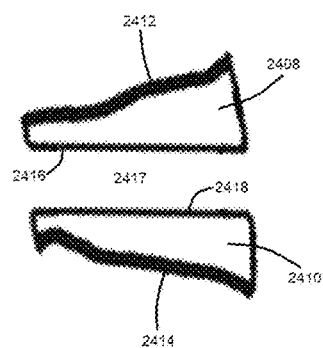

Based on the digital model 2406, two endplates may be printed using 3-D printing technologies. FIG. 24D shows a printed first endplate 2408 and second endplate 2410. The first endplate 2408 has an outer surface 2412 that matches a surface morphology of the superior vertebrae 2402 while the second endplate 2410 has an outer surface 2414 that matches a surface morphology of the inferior vertebrae 2404. The first endplate 2408 has a textured inner surface 2416 and the second endplate 2410 has a textured inner surface 2416 too. The texture may be any rough texture including, but not limited to, bumps (such as on the inner surface of the endplate of FIG. 18), a lattice structure (such as on the inner surface of the endplate of FIG. 15), a porous structure with many small nooks and crannies (similar to the friction details of FIG. 8), and the like. Texturing the first inner surface 2416 and the second inner surface 2418 increases the surface area of the inner surfaces, and greatly improves bonding with the core 2424 as will be discussed shortly.

The first inner surface 2410 and the second inner surface 2416 may be parallel to each other in order for the core 2424 to have a uniform thickness. The two endplates may be printed such that there is sufficient space 2417 for a core 2424 in between the first inner surface 2410 and the second inner surface 2416. The space 2417 for the core can be made thinner or thicker depending on preferred core 2424 thickness. The space 2817 for the core is preferably centered in between the first outer surface 2412 and the second outer surface 2414, but may be located at any point in between the endplates.

The first endplate 2408 and the second endplate 2410 are made of any biocompatible material, preferably a ceramic or a non-oxidizing metal. Such materials are hard and can withstand high heat without breaking or deforming, making them ideal injection molding core 2424 in between the endplates. The endplates may have gripping slots as previously described.

Figure 24E:
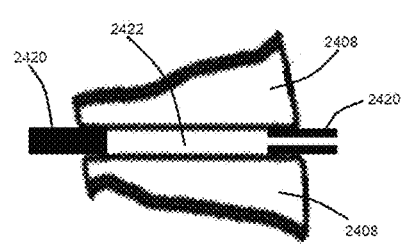

The core 2422 may be injection molded in between the endplates. In FIG. 24E, the first endplate 2408 is the top of the mold, the second endplate 2410 is the bottom of the mold. A cylindrical portion 2420 surrounds the core formation area 2422, creating an airtight seal around the core formation area 2422, apart from the injection valve.

Once the mold is ready, an elastomeric core 2424 is injection molded in between the endplates. The textured inner surfaces of the endplates readily absorb the core 2424 while it's still liquid during the start of the molding process. When the core 2424 cools and solidifies, it becomes permanently fused with the endplates. The first endplate 2408, core 2424, and the second endplate 2410 are firmly held together and form the artificial replacement disk assembly 2426.

Figure 24F:
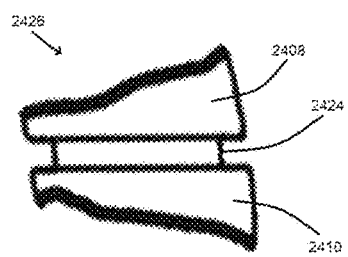
Figure 24G:
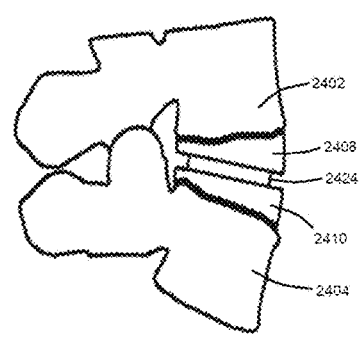

FIG. 24F shows the assembly 2426 implanted in between the superior vertebrae 2402 and the inferior vertebrae.

Figure 25:
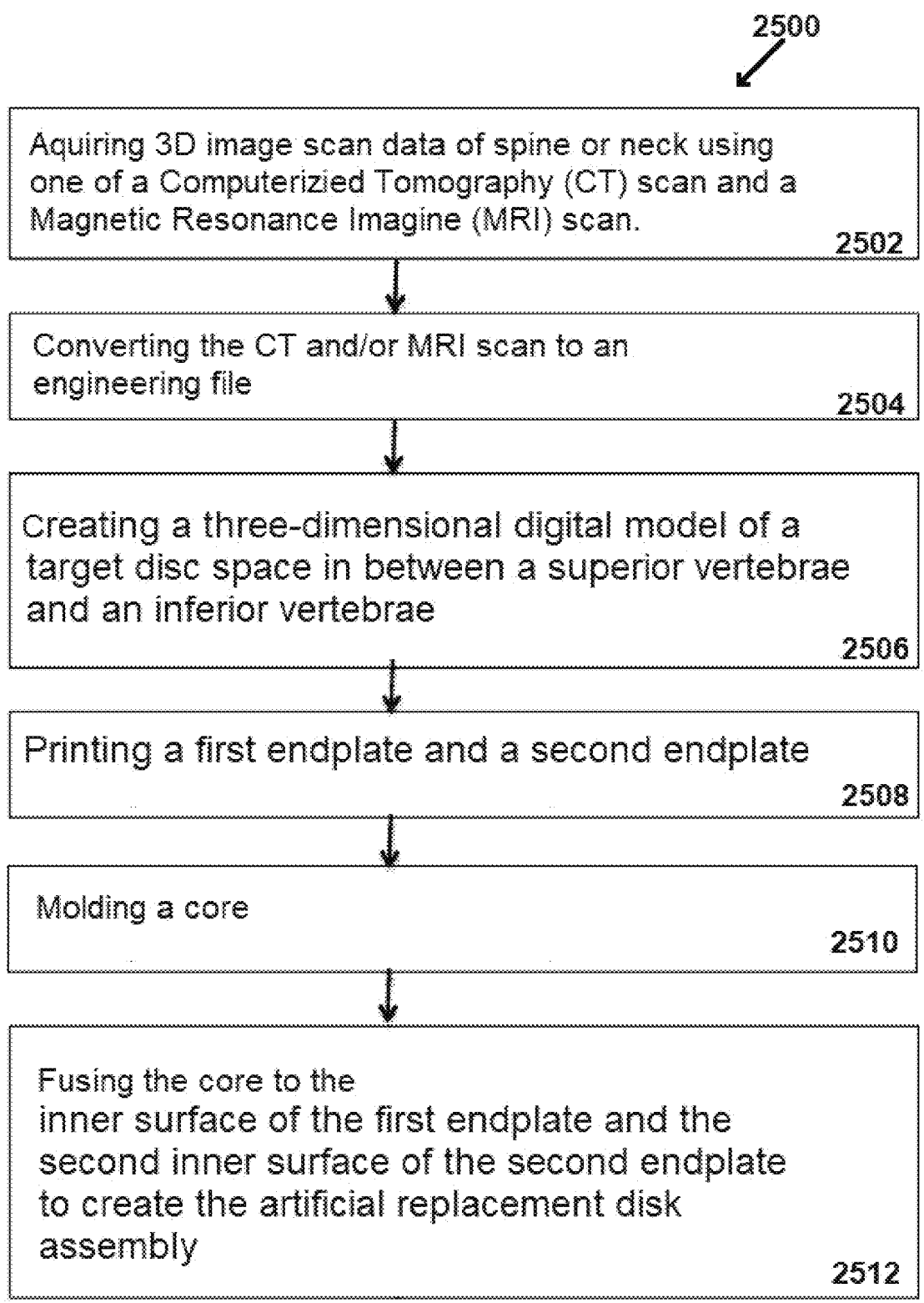
FIG. 25 is a schematic flowchart illustrating the steps of a method for manufacturing an artificial replacement disk assembly in accordance with the embodiments of the present invention.

Now referring to FIG. 25, one exemplary method 2500 of fabricating an artificial replacement disk comprises the steps of acquiring three-dimensional image scan data of spine or neck using at least one of computerized tomography (CT) scan and magnetic resonance imaging (MRI) 2502, converting the CT and/or MRI scan to an engineering file 2504, creating a three-dimensional digital model of a target disc space in between a superior vertebrae and an inferior vertebrae 2506, printing a first endplate and a second endplate 2508, molding a core 2510, fusing the core 2510 to the endplates to create the artificial replacement disk assembly 2512. This method 2500 is similar to the method of FIG. 23, but the core 2424 of the artificial replacement disk is not molded in between the endplates and the endplates do not require textured inner surfaces. Rather this core 2424 is molded inside of a mold that emulates the core formation area 2422, wherein the core 2424 still ends up matching the surface morphology of the inner surfaces of the endplates. Furthermore, this method 2500 involves the step of fusing the core to the endplates. Fusion may be achieved by using a glue or adhesive the bond the core in between the endplates. Alternatively, the core may be placed in between the inner surfaces of the endplates to form to form a subassembly. The subassembly is then subjected to ultrasonic vibrations to induce ultrasonic bonding at the inner surfaces of the endplates, fusing the core and the endplates together.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

The foregoing detailed description is merely exemplary in nature and is not intended to limit the invention or application and uses of the invention. Furthermore, there is no intention to be bound by any expressed or implied theory presented in the preceding technical field, background, brief summary, or the following detailed description.

The invention claimed is:

1. An artificial replacement disk assembly comprising:
   a first endplate configured to contact a superior vertebrae, wherein
      a first outer surface matches a first surface morphology of the superior vertebrae
      a first inner surface is textured;
   a second endplate configured to contact an inferior vertebrae, wherein
      a second outer surface matches a second surface morphology of the inferior vertebrae
      a second inner surface is textured; and
   a core binding the first endplate and the second endplate, wherein
      the core is fused to the first inner surface and the second inner surface; and
   wherein at least one of the first endplate and the second endplate comprise a plurality of slots, the plurality of slots including at least a first set of slots to receive a gripping tool in a first position and a second set of slots to receive the gripping tool in a second position.

2. The artificial replacement disk assembly of claim 1, wherein a three-dimensional model of a target disc space is modified to produce at least one of proper angle and spacing in between the superior vertebrae and the inferior vertebrae.

3. The artificial replacement disk assembly of claim 1, wherein the first and second endplates are made of a ceramic.

4. The artificial replacement disk assembly of claim 1, wherein the first and second endplates are made of a non-corrosive metal.

5. The artificial replacement disk assembly of claim 1, wherein the first and second inner surfaces are textured with a lattice pattern.

6. The artificial replacement disk assembly of claim 1, wherein
   a plurality of nubs protrude from the first and second inner surfaces;
   for each of the plurality of nubs:
      a width of a base of the nub is less than a widest portion of the nub body, taken along a plane perpendicular to the corresponding inner surface.

7. The artificial replacement disk assembly of claim 1, wherein the first and second inner surfaces are parallel.

8. A method for fabricating an artificial replacement disk assembly comprising:
  acquiring three-dimensional image scan data of spine or neck using at least one of computerized tomography (CT) scan and magnetic resonance imaging (MRI);
  converting the CT and/or MRI scan to an engineering file;
  creating a three-dimensional digital model of a target disc space in between a superior vertebrae and an inferior vertebrae;
  printing a first endplate and a second endplate, wherein
    a first outer surface of the first endplate matches a first surface morphology of the superior vertebrae,
    a first inner surface of the first endplate is textured,
    a second outer surface of the second endplate matches a second surface morphology of the inferior vertebrae,
    a second inner surface of the second endplate is textured,
    the first inner surface and the second inner surface are parallel,
    the first inner surface and the second inner surface are spaced to contain a core; and
  fusing a core to first inner surface and the second inner surface to create the artificial replacement disk assembly, wherein
    the core is in between the first endplate and the second endplate;
      the core binds the first endplate to the second endplate; and
  wherein at least one of the first endplate and the second endplate comprise a plurality of slots, the plurality of slots including at least a first set of slots to receive a gripping tool in a first position and a second set of slots to receive the gripping tool in a second position.

9. The method of claim 8, wherein the three-dimensional model of the target disc space is modified to produce at least one of proper angle and spacing in between the superior vertebrae and the inferior vertebrae.

10. The method of claim 8, wherein the first and second endplates are made of a ceramic.

11. The method of claim 8, wherein the first and second endplates are made substantially of aluminum oxide.

12. The method of claim 8, wherein the first and second endplates are made of a non-corrosive metal.

13. The method of claim 8, wherein the first and second inner surfaces are textured with a lattice pattern.

14. The method of claim 8, wherein the first and second inner surfaces are textured to be porous.

15. The method of claim 8, wherein the first and second inner surfaces are parallel.

16. The method of claim 8, wherein at least one of the first endplate and the second endplate have gripping structures configured to receive a gripping tool.

17. The method of claim 8, wherein the core is fused to the first inner surface and the second inner surface through injection molding.

18. The method of claim 8, wherein the core is fused to the first inner surface and the second inner surface through the use of adhesives.

19. The method of claim 8, wherein the core is fused to the first inner surface and the second inner surface through ultrasonic welding.

* * * * *